US008877955B2

(12) United States Patent
Burckhardt

(10) Patent No.: US 8,877,955 B2
(45) Date of Patent: Nov. 4, 2014

(54) SECONDARY AMINOSILANES

(71) Applicant: Sika Technology AG, Baar (CH)

(72) Inventor: Urs Burckhardt, Zürich (CH)

(73) Assignee: Sika Technology AG, Baar (CH)

( * ) Notice: Subject to any disclaimer, the term of this patent is extended or adjusted under 35 U.S.C. 154(b) by 0 days.

(21) Appl. No.: 13/919,636

(22) Filed: Jun. 17, 2013

(65) Prior Publication Data

US 2013/0281562 A1    Oct. 24, 2013

Related U.S. Application Data

(63) Continuation of application No. PCT/EP2011/072631, filed on Dec. 13, 2011.

(30) Foreign Application Priority Data

Dec. 17, 2010 (EP) ..................................... 10195811

(51) Int. Cl.

| | | |
|---|---|---|
| C07F 7/10 | (2006.01) | |
| C07F 7/18 | (2006.01) | |
| C08G 18/28 | (2006.01) | |
| C08G 73/02 | (2006.01) | |
| C08G 18/10 | (2006.01) | |
| C08G 18/75 | (2006.01) | |
| C08G 18/76 | (2006.01) | |
| C09J 175/04 | (2006.01) | |
| C08G 18/48 | (2006.01) | |

(52) U.S. Cl.
CPC ............ *C07F 7/1804* (2013.01); *C08G 18/289* (2013.01); *C08G 73/0246* (2013.01); *C08G 18/10* (2013.01); *C08G 18/755* (2013.01); *C08G 18/765* (2013.01); *C07F 7/1836* (2013.01); *C09J 175/04* (2013.01); *C08G 18/4866* (2013.01)
USPC ........... 556/424; 525/453; 556/413; 556/414; 556/419

(58) Field of Classification Search
None
See application file for complete search history.

(56) References Cited

U.S. PATENT DOCUMENTS

| | | | |
|---|---|---|---|
| 3,033,815 A | 5/1962 | Pike | |
| 3,676,478 A | 7/1972 | Golitz et al. | |
| 4,067,844 A | 1/1978 | Barron et al. | |
| 5,364,955 A | 11/1994 | Zwiener et al. | |
| 6,197,912 B1 | 3/2001 | Huang et al. | |
| 7,238,768 B2 * | 7/2007 | Hupfield et al. | 528/38 |
| 7,906,673 B2 * | 3/2011 | Burckhardt | 556/465 |

FOREIGN PATENT DOCUMENTS

EP    0 256 643 A2    2/1988

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) issued on Jun. 27, 2013, in the corresponding International Application No. PCT/EP2011/072631. (7 pages).
International Search Report (PCT/ISA/210) issued on Jan. 16, 2012, by the European Patent Office as the International Searching Authority for International Application No. PCT/EP2011/072631.
Written Opinion (PCT/ISA/237) issued on Jan. 16, 2012, by the European Patent Office as the International Searching Authority for International Application No. PCT/EP2011/072631.

* cited by examiner

*Primary Examiner* — Marc Zimmer
(74) *Attorney, Agent, or Firm* — Buchanan Ingersoll & Rooney PC

(57) ABSTRACT

The present disclosure invention relates to novel secondary aminosilanes, a method for producing same, and the use thereof. The secondary aminosilanes can be produced from readily available reactants in a simple manner. The secondary aminosilanes are characterized for example by a low viscosity and are well suited for producing silane-functional polymers that have a low viscosity, fast curing, and good thermal stability.

20 Claims, No Drawings

SECONDARY AMINOSILANES

RELATED APPLICATION(S)

This application claims priority as a continuation application under 35 U.S.C. §120 to PCT/EP2011/072631, which was filed as an International Application on Dec. 13, 2011 designating the U.S., and which claims priority to European Application 10195811.4 filed in Europe on Dec. 17, 2010. The entire contents of these applications are hereby incorporated by reference in their entireties.

FIELD

The present disclosure relates to secondary amines and to their use, for example, as adhesives and crosslinking agents, and as building components of silane functional polymers; as well as to curable materials, such as silane crosslinking curable materials, and to their use, for example, as casting compounds, sealants, adhesives, coverings, coatings, and paints.

BACKGROUND INFORMATION

Organosiloxanes comprising amino groups, referred to as aminosilanes in short, are used as adhesion agents, as crosslinking agents for curable materials as well as building components of silane functional polymers, among other uses. Owing to the ease of their manufacture, aminosilanes having primary amino groups ("primary aminosilanes") are very common; however, they can have several drawbacks when used. Owing to the relatively hydrophilic primary group, they can have undesired moisture absorbing properties, which can have a negative effect on the adhesion of a cured composition, which is exposed to moisture, to the substrate. In the use of silane functional polymers as building components, polymers which are prepared by the addition reaction of isocyanate functional polyurethane polymers to aminosilanes, primary aminosilanes can lead to high viscosities, can make it difficult to process the silane functional polymers, and can worsen the application properties as well as the ductility of the products prepared therefrom. Therefore, it can be advantageous to use, instead of the primary aminosilanes, those that have secondary amino groups ("secondary aminosilanes"); they are hydrophobic and they lead to low viscosity, silane functional polyurethane polymers. However, the availability of cost effective and stockable secondary amines is limited. The silane crosslinking polyurethanes produced from the secondary aminosilanes that are known can take a long time to cure, and can often have a low resistance to heating.

It is known to prepare secondary aminosilanes by hydrosilylation of allylsilanes, as described in U.S. Pat. No. 6,197, 912, for example, or by nucleophilic substitution of chloro- or bromoalkylsilanes with primary amines, or of alkyl- or aryl halides with primary aminosilanes, as described in U.S. Pat. No. 3,676,478 or U.S. Pat. No. 6,197,912, for example. Due to the expensive manufacture and the much smaller quantities in comparison to the primary aminosilanes, they are considerably more expensive than the primary aminosilanes.

Therefore, for the manufacturers of silane functional polymers, it can be more advantageous to produce secondary aminosilanes starting from primary aminosilanes. The addition reaction with Michael acceptors, for example, acrylonitrile, acrylic acid ester, and maleic acid ester, is known, and has been described in U.S. Pat. No. 3,033,815, U.S. Pat. No. 4,067,844 and U.S. Pat. No. 5,364,955, for example. These reagents are inexpensive, and the reaction to form the secondary aminosilane succeeds already under mild conditions. However, it can be slow and incomplete, thus leaving a portion of the Michael acceptors in an unadducted form, which may involve their subsequent removal, if one wishes to prevent interfering odors of the products produced with the addition products. The Michael adducts of primary aminosilanes can include additional functional groups, such as cyano groups, and for example ester groups. The presence of ester groups leads to silane functional polyurethane polymers having a relatively low viscosity. However, this is associated with an issue whereby the ester groups are capable of reacting with primary or secondary amino groups, and in the process they form amides. In silane crosslinking curable materials, which can be formulated with primary amines and aminosilanes as catalysts and adhesives, this can be undesirable, because it can lead to the deactivation of the amines and to an increased crosslinking density and thus to increased brittleness of the cured polymer. Due to the creeping self condensation to form polyamides, incompletely alkylated aminosilanes with ester groups are also often unsuitable for storage.

SUMMARY

An aminosilane is disclosed of formula (I)

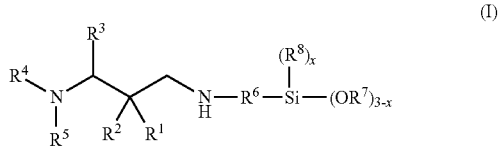

where
R$^1$ and R$^2$ either
each stand, independently of each other, for a monovalent hydrocarbon residue having 1-12 C atoms,
or together they stand for a bivalent hydrocarbon residue having 4-12 C atoms, which is part of an optionally substituted carbocyclic ring having 5-8, 6, C atoms;
R$^3$ stands for a hydrogen atom or for an alkyl group or arylalkyl group or alkoxycarbonyl group each having 1-12 C atoms;
and either
R$^4$ stands for a monovalent aliphatic, cycloaliphatic or arylaliphatic residue having 1-20 C atoms, which optionally contains heteroatoms, and
R$^5$ stands for a hydrogen atom or for a monovalent, aliphatic, cycloaliphatic or arylaliphatic residue having 1-20 C atoms, which optionally contains heteroatoms,
or
R$^4$ and R$^5$ together stand for a bivalent aliphatic residue having 3-30 C atoms, which is part of an optionally substituted heterocyclic ring having 5-8, wherein this ring optionally contains further heteroatoms, besides a nitrogen atom;
R$^6$ stands for a linear or branched alkylene or cycloalkylene residue having 1-20 C atoms, optionally with aromatic portions, and optionally with one or more heteroatoms;
R$^7$ stands for an alkyl group having 1-10 C atoms, which optionally comprises ether oxygen, and two OR$^7$ groups together can stand for a bivalent glycolate group which forms a ring with the silicon atom;
R$^8$ stands for an alkyl group having 1-8 C atoms; and
x stands for 0, 1 or 2.

A method is disclosed for manufacturing an iminosilane of formula (II):

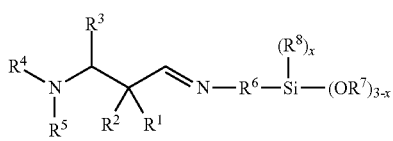
(II)

wherein at least one aminosilane AS of formula (III) is condensed with at least one aldehyde ALD of formula (IV), wherein formula (III) and formula (IV) are as follows:

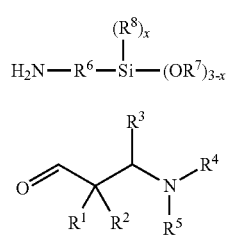

(III)

(IV)

An adduct AD is disclosed, comprising: a reaction of at least one aminosilane of formula (I):

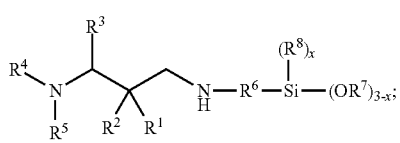

(I)

and at least one compound VB which carries at least one reactive group RG, wherein the reactive group RG is selected from a group consisting of: isocyanate, isothiocyanate, cyclocarbonate, epoxide, episulfide, aziridine, acryl, methacryl, 1-ethinylcarbonyl, 1-propinylcarbonyl, maleimide, citraconimide, vinyl, isopropenyl and allyl groups.

A compound is disclosed, comprising at least one silanol group of formula (IX), obtained from at least partial hydrolysis of at least one aminosilane of formula (I):

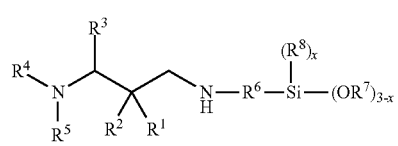

(I)

or of at least one iminosilane of formula (II):

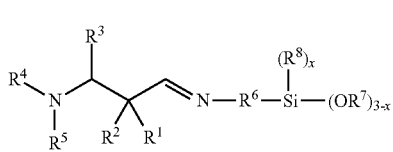

(II)

or of at least one adduct AD which includes a reaction of at least one aminosilane of formula (I); and at least one compound VB which carries at least one reactive group RG, wherein the reactive group RG is selected from a group consisting of: isocyanate, isothiocyanate, cyclocarbonate, epoxide, episulfide, aziridine, acryl, methacryl, 1-ethinylcarbonyl, 1-propinylcarbonyl, maleimide, citraconimide, vinyl, isopropenyl and allyl groups, and wherein formula (IX) is as follows:

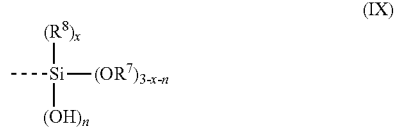

(IX)

where n stands for 1 or 2 or 3, with a condition that n has at most a value (3-x).

DETAILED DESCRIPTION

The present disclosure encompasses production of novel secondary aminosilanes which can have an advantageous property when used as adhesives and crosslinking agents as well as building components of silane functional polymers. They can be produced by an exemplary simple method, they can be liquid, and they can have a low viscosity at room temperature. For example, they can make it possible to provide silane function polymers that have a low viscosity, cure rapidly, and have a good thermal resistance.

It was found surprisingly that such features can be achieved with secondary aminosilanes as disclosed herein. At room temperature, they can be liquid and have a relatively low viscosity, while nevertheless having a low volatility and little odor. They can be manufactured from commercial primary aminosilanes and from special aldehydes having a secondary or tertiary amino group in a simple process which does not require expensive processing steps. Exemplary advantageous properties, such as the rapid hydrolysis rate of the silane groups, the good compatibility in many curable materials, and the particularly good adhesion promoting properties can for example be explained by the presence of the additional amino group originating from the aldehyde. Exemplary secondary aminosilanes disclosed herein can have particularly advantageous properties when used to manufacture silane functional polymers by adding isocyanate functional polyurethane polymers in an addition reaction. Silane crosslinking curable materials that contain such silane functional polymers can have a relatively low viscosity, they can cure rapidly and completely in contact with moisture, and they can have an excellent thermal resistance which is substantially better than that of similar previous known systems manufactured with secondary aminosilanes.

The subject matter disclosed herein includes an exemplary aminosilane of formula (I) as follows:

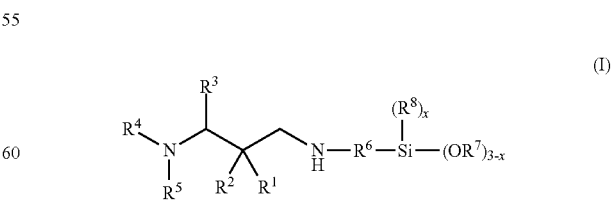

(I)

where
$R^1$ and $R^2$ either
each stand, independently of each other, for a monovalent hydrocarbon residue having 1-12 C atoms, or together they stand for a bivalent hydrocarbon residue having 4-12 C atoms, which is part of an optionally substituted carbocyclic ring having 5-8, preferably for example 6, C atoms;

$R^3$ stands for a hydrogen atom or for an alkyl group or arylalkyl group or alkoxycarbonyl group each having 1-12 C atoms;

and either $R^4$ stands for a monovalent aliphatic, cycloaliphatic or arylaliphatic residue having 1-20 C atoms, which optionally contains heteroatoms, and $R^5$ stands for a hydrogen atom or for a monovalent, aliphatic, cycloaliphatic or arylaliphatic residue having 1-20 C atoms, which optionally contains heteroatoms, or $R^4$ and $R^5$ together stand for a bivalent aliphatic residue having 3-30 C atoms, which is part of an optionally substituted heterocyclic ring having 5-8, preferably for example 6 ring atoms, wherein this ring optionally contains further heteroatoms, besides a nitrogen atom;

$R^6$ stands for a linear or branched alkylene or cycloalkylene residue having 1-20 C atoms, optionally with aromatic portions, and optionally with one or more heteroatoms, such as nitrogen atoms;

$R^7$ stands for an alkyl group having 1-10 C atoms, which optionally comprises ether oxygen;

$R^8$ stands for an alkyl group having 1-8 C atoms; and x stands for 0, 1 or 2.

Two $OR^7$ groups together can stand for a bivalent glycolate group which forms a ring with the silicon atom.

The term "secondary aminosilane" denotes for example, an organoalkoxysilane, the residue of which that is bound directly to the silicon atom comprises at least one secondary amino group. The term "primary aminosilane" denotes for example, an organoalkoxysilane, the residue of which that is bound to the silicon atom comprises at least one primary amino group. The term "iminosilane" denotes for example an organoalkoxysilane, the residue of which that is bound directly to the silicon atom comprises at least one imino group.

The term "organoalkoxysilane," for short "silane," denotes for example a silicon containing compound, in which the silicon atom carries at least one, (for example two or three), alkoxy group groups, and it also carries a directly bound organic residue and thus comprises at least one Si—C bond. The term "silane group" denotes for example the silicon containing group bound to the organic residue of an organoalkoxysilane.

The term "primary amino group" denotes for example an $NH_2$ group which is bound to an organic residue, and the term "secondary amino group" denotes for example an NH group which is bound to two organic residues, which can also be a common portion of a ring, and the term "tertiary amino group" denotes an amino group, the nitrogen atom ("tertiary amine nitrogen") of which is bound to three organic residues, wherein two of these residues also can be a common portion of a ring.

The term "silane crosslinking" is used to denote for example a curable material, wherein a ("silane functional") polymer, that is a polymer which comprises silane groups, can be cured primarily by reacting the silane groups with moisture.

The term "aliphatic" is used to denote for example an amine or an isocyanate, if the amino or isocyanate groups thereof are each bound to aliphatic, cycloaliphatic or arylaliphatic residues; accordingly, the functional groups thereof are referred to as aliphatic amino or aliphatic isocyanate groups.

The term "aromatic" is used to denote for example an amine or an isocyanate, if the amino or isocyanate groups thereof are each bound to an aromatic residue; accordingly, the functional groups thereof are referred to as aromatic amino or aromatic isocyanate groups.

The term "curable material" comprises liquid or meltable reactive organic materials and compositions thereof, which are manufactured at least partially synthetically, and which alone and/or as a result of contact with air can be cured to plastics and plastic compositions.

The term "polymer" comprises an assembly of chemically uniform macromolecules that differ, however, in terms of their polymerization degree, molecular weight and chain length, said assembly having been manufactured by a polyreaction (polymerization, polyaddition, polycondensation). The term also includes derivatives of such a collective of macromolecules from polyreactions, that is compounds which were obtained by reactions, such as, for example, additions or substitutions, of functional groups on predetermined macromolecules, and which may or may not be chemically uniform. The term comprises moreover also so-called prepolymers, that is to say reactive oligomer preadducts, the functional groups of which participate in the building of macromolecules.

The term "polyurethane" comprises all polymers that are manufactured by the so-called diisocyanate polyaddition method. Thus, polyurethanes can comprise urethane or thiourethane groups and for example also urea groups. However, the term polyurethane also includes polymers which are nearly or entirely free of urethane groups. They are for example the so-called polyureas, polyether polyureas, and polyester polyureas, as well as moreover polyether polyurethanes, polyester polyurethanes, polyisocyanurates, and polycarbodiimides.

The term "poly" at the beginning of substance names, such as polyamine, polyol or polyepoxide, is used to denote for example substances that contain formally two or more of the functional groups occurring in their name, per molecule.

The term "polyisocyanate" comprises compounds having two or more isocyanate groups, regardless of whether they are monomer di- or triisocyanates, oligomer diisocyanates, or adducts and polymers comprising isocyanate groups.

The designation used in bold print, such as AS, ALD, Y1, Y2, C, AD, VB, RG, SP, PUP, S1, S2 or the like are used only to improve the readability and the identification.

The expression "room temperature" is used to denote an exemplary temperature of 23° C.

$R^1$ and $R^2$ each, for example, stand for a methyl residue.

$R^3$ stands for, for example, a hydrogen atom.

Thus, $R^1$ and $R^2$ can each stand for a methyl residue and/or $R^3$ can stand for a hydrogen atom.

It can, for example, be preferable for $R^4$ to stand for methyl, ethyl, propyl, isopropyl, butyl, 2-ethylhexyl, cyclohexyl, 2-hydroxyethyl, 2-hydroxypropyl, 2-methoxyethyl or benzyl, and for $R^5$ to stand for hydrogen or methyl, ethyl, propyl, isopropyl, butyl, 2-ethylhexyl, cyclohexyl, 2-hydroxyethyl, 2-hydroxypropyl, 2-methoxyethyl or benzyl.

Moreover, it can, for example, be preferable for $R^4$ and $R^5$ together to form—including the nitrogen atom—a ring, particularly a pyrrolidine, piperidine, morpholine or N-alkylpiperazine ring, wherein this ring or the alkyl group are optionally substituted.

It can, for example, be preferable for $R^6$ to stand for a linear or branched alkylene residue having 1-6 C atoms, in particular for a propylene group.

Moreover, $R^6$ can, for example, preferably stand for a linear alkylene residue having 5-7 C atoms, which comprises one or 2 secondary amino groups in the chain, such as for a —$(CH_2)_2$—NH—$(CH_2)_3$— or for a —$(CH_2)_2$—NH—$(CH_2)_2$—NH—$(CH_2)_3$— residue.

$R^7$ can, for example, preferably stand for a methyl or for an ethyl or for an isopropyl group, in particular for a methyl or for an ethyl group.

It can, for example, be preferable for $R^8$ to stand for a methyl or for an ethyl group, such as for a methyl group.

x can, for example, preferably stand for 0 or for 1, in particular for 0.

A further exemplary subject matter of the present disclosure encompasses an iminosilane of formula (II):

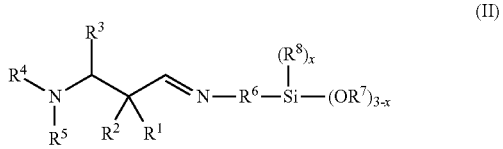

(II)

In formula (II), $R^1$, $R^2$, $R^3$, $R^4$, $R^5$, $R^6$, $R^7$, $R^8$ and x have the already mentioned definitions.

For the manufacture of an aminosilane of formula (I), an iminosilane of formula (II) can be hydrogenated. This hydrogenation can take place directly with molecular hydrogen or indirectly by hydrogen transfer from other reagents. Examples of such reagents are formic acid, wherein $CO_2$ is released (based on a Leuckart-Wallach reaction); cyclohexene, which is dehydrogenated in the process to benzene, as well as other alkenes, such as limonene; organosilanes; alkali metals in protic solvents; or hydrazine in the presence of an oxidation agent. The term "hydrogenation" here also covers the reduction by means of hydrides, such as lithium aluminum hydride, sodium borohydride and sodium bis(2-methoxyethoxy)aluminum hydride (Vitride®, Red-Al®), for example. The hydrogenation with molecular hydrogen is, for example, preferred.

The hydrogen required for the hydrogenation can, for example preferably be used at an increased pressure, such as at 5-250 bar, and an increased temperature, such as 20-160° C., in the presence of a suitable catalyst. Here, the conditions can be advantageously selected in such a manner that, on the one hand, the imino groups are hydrogenated as completely as possible, and, on the other hand, as few components of the imine of formula (IV) are hydrogenated or decomposed.

Suitable catalysts for the hydrogenation are homogeneous catalysts, such as, rhodium, ruthenium or iridium complexes, for example, in particular heterogeneous catalysts, such as platinum, palladium, rhodium, ruthenium, osmium, rhenium, nickel, cobalt or iron, for example, as well as the compounds or preparations thereof on support materials, wherein particularly suitable support materials include pumice, diatomaceous earth, aluminum, silica gel or activated charcoal. It can be particularly suitable to use palladium on carbon (Pd/C), platinum on carbon (Pt/C), Adams catalyst and Raney nickel. Palladium on carbon and platinum on carbon are, for example, preferred.

The reductive alkylation is, for example, preferably carried out in the liquid phase. It can be carried out, as desired, without solvent or in the presence of a solvent, wherein suitable solvents are inert under the reaction conditions. Particularly suitable solvents include $C_1$-$C_{10}$ alkanes, such as hexane, heptane or cyclohexane, for example, and alcohols, in particular primary $C_1$-$C_6$ alcohols, such as methanol or ethanol, but also secondary alcohols, such as isopropanol and tertiary alcohols, such as tert-butanol. When using an alcohol as solvent, it is, for example, preferable to use the alcohol released during the hydrolysis of the silane groups; that is, for example, methanol if a methoxysilane is used, or ethanol if an ethoxysilane is used.

The hydrogenation can be carried out in batches or in a continuous process, for example, in a continuously running hydrogenation apparatus. In an exemplary process, at least one iminosilane of formula (II), optionally in solution, is mixed under pressure continuously with hydrogen, and passed through an appropriate catalyst. The hydrogen here can be generated continuously by water electrolysis.

If desired, the aminosilane of formula (I) can be purified after the manufacture, for example, by distillation.

An iminosilane of formula (II) is obtained by an exemplary method of manufacture in which at least one aminosilane AS of formula (III) is condensed with at least one aldehyde ALD of formula (IV). The reactants can here be in the free or in a derivatized form. Formula (III) and formula (IV) are as follows:

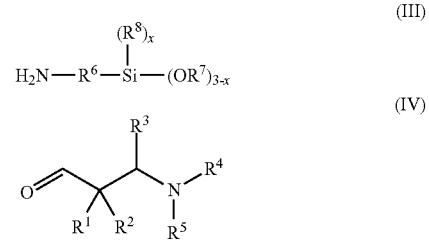

In formulas (III) and (IV), $R^1$, $R^2$, $R^3$, $R^4$, $R^5$, $R^6$, $R^7$, $R^8$ and x have the already mentioned definitions.

The aldehyde ALD can be used in the stoichiometric quantity, or in a stoichiometric excess with respect to the aminosilane AS.

Such condensation reactions between primary amines and aldehydes are known. For the manufacture of an iminosilane of formula (II), an aminosilane is used in the present case as an exemplary primary amine. This entails the additional issue that the water released during the condensation can lead to a hydrolysis of silane groups. However, this can be undesirable and, in exemplary embodiments, should be largely suppressed to obtain a qualitatively good product. Otherwise, under the renewed release of water, condensation products can form, such as organosiloxanes; that is, in the present case, molecules which can consist of two or more immunosilanes bound via siloxane groups. For the manufacture of an iminosilane of formula (II) of good quality, it can be advantageous to select a manufacturing method in which the hydrolysis of the silane groups is largely suppressed, in order to obtain, after the hydrogenation thereof, aminosilanes of formula (I) of good quality.

For the manufacture of an iminosilane of formula (II) by the condensation of an aminosilane AS of formula (III) with an aldehyde ALD of formula (IV), it can be preferable to use a method in which the aminosilane AS is used as starting material, and the aldehyde ALD is added. Here, it can be advantageous to ensure that, already during the conversion, the water formed is removed from the reaction mixture, for example, by the permanent application of a vacuum which immediately suctions off water released by the condensation, or by removing said water by means of a water absorbing substance, such as an appropriate molecular sieve, for example. The reaction can be carried out at exemplary temperatures of 5-250° C. It is, for example, preferable to use a reaction temperature in the range of 20-100° C.

Such reactions can be carried out in the presence of a solvent which forms an azeotrope with water, wherein the water together with the solvent is removed from the reaction mixture. However, it is, for example, preferable to manufacture the iminosilane of formula (II) using the alcohol released during the hydrolysis of the silane groups, that is, for example, methanol if a methoxysilane is used, or ethanol if an ethoxysilane is used. It was observed that, if the aminosilane AS is used as starting substance in the corresponding alcohol, and the aldehyde ALD is added dropwise with immediate removal of the water, iminosilanes of formula (II) of excellent quality are obtained. However, it is also possible to obtain iminosilanes of formula (II) of good quality by entirely omitting the use of solvents during their manufacture. In the process, the aminosilane AS is used as starting substance, and the aldehyde ALD is added in a vacuum.

Moreover, an iminosilane of formula (II) can also be produced by an exemplary indirect path as a product of a transimination reaction. For this purpose, first an intermediate product in the form of an imine of formula (Va) is produced, by reacting at least one aldehyde ALD of formula (IV) with a small, relatively volatile, primary monoamine, wherein the water produced in the condensation is removed as completely as possible using a suitable procedure. Subsequently, the largely anhydrous intermediate product is reacted with at least one aminosilane AS of formula (III) at increased temperature and reduced pressure with transimination to produce the aminosilane of formula (I), wherein the small, relatively volatile, primary monoamine is continuously removed by vacuum from the reaction mixture.

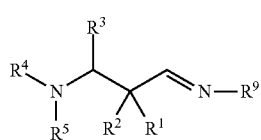

(Va)

In formula (V a), $R^9$ stands, for example, for the alkyl residue of a small, relatively volatile, primary monoamine, preferably for example an alkyl group having 1-6 C atoms, such as for a propyl, isopropyl or butyl group, and $R^1$, $R^2$, $R^3$, $R^4$ and $R^5$ have the already mentioned definitions.

Moreover, an iminosilane of formula (II) can also be obtained particularly by an indirect path via an intermediate product in the form of an acetal of formula (Vb).

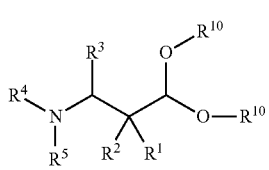

(Vb)

In the formula (Vb)

$R^{10}$ stands, for example, for the alkyl residue of a small, relatively volatile alcohol, preferably for example, an alkyl group having 1-6 C atoms, such as for a methyl, ethyl or isopropyl group, and $R^1$, $R^2$, $R^3$, $R^4$ and $R^5$ have the already mentioned definitions.

For the manufacture of an acetal of formula (Vb), the aldehyde ALD of formula (IV) can be condensed with a small, relatively volatile alcohol, wherein the water released in the process is removed as completely as possible using a suitable procedure. Subsequently, the largely anhydrous intermediate product is reacted with at least one aminosilane AS of formula (III) at increased temperature and reduced pressure to produce the aminosilane of formula (I), optionally in the presence of a catalyst, wherein the small, relatively volatile alcohol is removed continuously by vacuum from the reaction mixture.

In the case where, in the reaction with the acetal of formula (Vb), an aminosilane AS with methoxysilane groups is used, that is $R^7$ in formula (III) stands for methyl, it can be preferable to use methanol as a relatively volatile alcohol for the acetate formation, and, in the corresponding case with ethoxysilane groups, it can be preferable to use ethanol for the manufacture of the acetal.

Both the manufacture via an acetal and also the manufacture via a transimination are in fact slightly more involved than the direct condensation, but both can have an advantage that the water that forms in each case can be removed before it comes in contact with silane groups potentially causing an undesired hydrolysis of the silane groups.

However, the manufacture of an aminosilane of formula (I) is also possible by reacting at least one aminosilane AS of formula (III) with at least one aldehyde ALD of formula (IV) in a one-pot reaction under hydrogenation, without isolating the corresponding iminosilane of formula (II). For example, the aminosilane AS can be used as starting substance in an appropriate solvent in the presence of a molecular sieve and then the aldehyde ALD is added dropwise, and finally—optionally after removal of the molecular sieve—the reaction solution is hydrogenated using an appropriate method.

Suitable as aminosilane AS of formula (III) are for example the following primary aminosilanes:

3-aminopropyltrimethoxysilane, 3-aminopropyldimethoxymethylsilane, 3-amino-2-methylpropyltrimethoxysilane, 4-aminobutyltrimethoxysilane, 4-aminobutyldimethoxymethylsilane, 4-amino-3-methylbutyltrimethoxysilane, 4-amino-3,3-dimethylbutyltrimethoxysilane, 4-amino-3,3-dimethylbutyldimethoxymetyylsilane, 2-aminoethyltrimethoxysilane, 2-aminoethyldimethoxymethylsilane, aminomethyltrimethoxysilane, aminomethyldimethoxymethylsilane, aminomethylmethoxydimethylsilane, 7-amino-4-oxaheptyldimethoxymethylsilane as well as their analogs with ethoxy or isopropoxy groups instead of the methoxy groups on the silicon;

so-called diaminosilanes, which carry besides a primary amino group, a secondary amino group (NH group), which is for example in the y position relative to the silicon atom, such as, in particular, N-(2-aminoethyl)-3-aminopropyltrimethoxysilane, N-(2-aminoethyl)-3-aminopropylmethyldimethoxysilane, N-(2-aminoethyl)-3-aminopropyltriethoxysilane, and N-(2-aminoethyl)-3-aminopropyltriisopropoxysilane; and so-called triaminosilanes, which carry besides a primary amino group, two secondary amino groups (NH groups), such as, in particular, N-(2-aminoethyl)-N'-[3-(trimethoxysilyl)propyl]ethylenediamine.

It can be preferable to use the aminosilane AS of formula (III), selected from the group consisting of 3-aminopropyltrimethoxysilane, 3-aminopropyltriethoxysilane, 4-amino-3,3-dimethylbutyltrimethoxysilane, N-(2-aminoethyl)-3-aminopropyltrimethoxysilane, and N-(2-aminoethyl)-3-aminopropyltriethoxysilane.

As aldehyde ALD of formula (IV) it is suitable to use, for example, the products of a Mannich reaction-like α-aminoalkylation, as known from the specialty literature. An aldehyde Y1 of formula (VI), an aldehyde Y2 of formula (VII), and a primary or secondary aliphatic amine C of formula (VIII) are reacted in the process, with splitting off of water, to an aldehyde ALD of formula (IV).

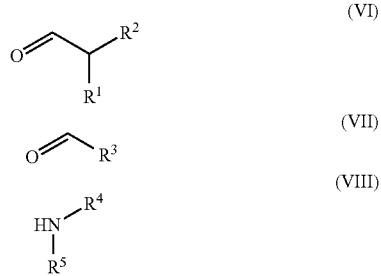

In the formulas (VI), (VII), and (VIII), $R^1$, $R^2$, $R^3$, $R^4$ and $R^5$ have the already mentioned definitions.

This reaction can be carried out either with the free reagents Y1, Y2, and C according to formulas (VI), (VII), and (VIII), or the reagents can be used partially or completely in a derivatized form. In an exemplary preferred embodiment, the reaction is carried out with all the reagents in free form as a one-pot reaction, and after completion of the reaction the aldehyde ALD is purified by distillation. In the process, it can be preferable not to use organic solvents.

Suitable as aldehyde Y1 of formula (VI) are, for example, isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde, and diphenylacetaldehyde. It can be preferable to use isobutyraldehyde.

Suitable as aldehyde Y2 of formula (VII) are, for example, formaldehyde, acetaldehyde, propionaldehyde, butyraldehyde, isobutyraldehyde, phenylacetaldehyde, and glyoxylic acid ester, in particular glyoxyl acid ethyl ester. It can be preferable to use formaldehyde.

Suitable as amine C of formula (VIII) are, for example, methylamine, dimethylamine, ethylamine, diethylamine, propylamine, dipropylamine, isopropylamine, diisopropylamine, butylamine, dibutylamine, isobutylamine, diisobutylamine, sec-butylamine, di-sec-butylamine, hexylamine, dihexylamine, 2-ethylhexylamine, di-(2-ethylhexyl)amine, octylamine, decylamine, dodecylamine, ethanolamine, diethanolamine, isopropanolamine, diisopropanolamine, cyclohexylamine, dicyclohexylamine, N-methylbutylamine, N-ethylbutylamine, N-methylcyclohexylamine, N-ethylcyclohexylamine, bis-(2-methoxyethyl)amine, pyrrolidine, piperidine, benzylamine, N-methylbenzylamine, N-isopropylbenzylamine, N-tert-butylbenzylamine, dibenzylamine, morpholine, 2,6-dimethylmorpholine, bis-(3-dimethylaminopropyl)amine, N-methyl- or N-ethylpiperazine, as well as moreover alkoxylates of primary amines, such as 2-(N-ethylamino)ethanol and 2-(N-propylamin)ethanol. It is preferable to use methylamine, dimethylamine, ethylamine, diethylamine, isopropylamine, diisopropylamine, butylamine, dibutylamine, isobutylamine, diisobutylamine, hexylamine, 2-ethylhexylamine, cyclohexylamine, N-methylcyclohexylamine, N-methylbenzylamine, N-isopropylbenzylamine, N-tert-butylbenzylamine, benzylamine, dibenzylamine, pyrrolidine, piperidine, morpholine, and 2,6-dimethylmorpholine. It can be particularly preferable to use methylamine, dimethylamine and particularly morpholine.

Piperazine is also suitable as amine C. In the case of piperazine, aldehydes ALD in the form of dialdehydes form, for example, which can be used in the reaction with aminosilanes AS in an exemplary molar ratio 1:2 for the manufacture of aminosilanes of formula (I) with two silane groups and with at least two secondary amino groups.

An exemplary preferred aldehyde ALD of formula (IV) can be selected from the group, comprising (e.g., consisting of): 2,2-dimethyl-3-methylaminopropanal, 2,2-dimethyl-3-dimethylaminopropanal, 2,2-dimethyl-3-ethylaminopropanal, 2,2-dimethyl-3-diethylaminopropanal, 2,2-dimethyl-3-bis(2-methoxyethyl)aminopropanal, 2,2-dimethyl-3-butylaminopropanal, 2,2-dimethyl-3-dibutylaminopropanal, 2,2-dimethyl-3-hexylaminopropanal, 2,2-dimethyl-3-(2-ethylhexyl)aminopropanal, 2,2-dimethyl-3-dodecylaminopropanal, 2,2-dimethyl-3-(N-pyrrolidino)propanal, 2,2-dimethyl-3-(N-piperidino)propanal, 2,2-dimethyl-3-(N-morpholino)propanal, 2,2-dimethyl-3-(N-(2,6-dimethyl)morpholino)propanal, 2,2-dimethyl-3-benzylaminopropanal, 2,2-dimethyl-3-(N-benzylmethylamino)propanal, 2,2-dimethyl-3-(N-benzylisopropylamino)propanal, 2,2-dimethyl-3-cyclohexylaminopropanal, 2,2-dimethyl-3-(N-cyclohexylmethylamino)propanal and N,N'-bis(2,2-dimethyl-3-oxopropyl)piperazine.

The aminosilanes of formula (I) can be stored with exclusion of moisture. The iminosilanes of formula (II) can also be stored with exclusion of moisture.

The silane groups of the aminosilanes of formula (I) and the silane groups of the iminosilanes of formula (II) have the property of hydrolyzing when they come in contact with moisture. In the process, organosilanes (silicon organic compounds containing one or more silanol groups, Si—OH groups) form, and, as a result of the subsequent condensation reactions, organosiloxanes (silicon organic compounds containing one or more siloxane groups, Si—O—Si groups) form, wherein the corresponding alcohol is released, for example, methanol in the case of methoxysilane groups or ethanol in the case of ethoxysilane groups.

In the—at least partial—hydrolysis of at least one aminosilane of formula (I) or of at least one iminosilane of formula (II), compounds with at least one silanol group of formula (IX) are obtained:

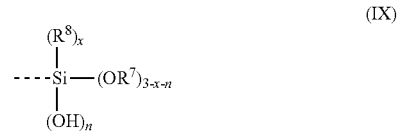

In the formula (IX), n stands, for example, for 1 or 2 or 3, with the condition that n has at most the value (3-x). $R^7$ and $R^8$ and x have the already indicated definitions.

The broken lines in the formulas in this document in each case represent the bond between a substituent and the associated molecule residue.

Such hydrolyzed or partially hydrolyzed compounds with silanol groups of formula (IX) are highly reactive and they can continue to react at a very high rate, either by condensation with additional silanol groups with formation of siloxane groups (Si—O—Si groups) or, for example, by condensation with hydroxyl groups of a substrate.

Both the aminosilanes of formula (I) and also the iminosilanes of formula (II) have the capacity to establish a strong adhesion to various substrates, or to improve the buildup of adhesion of compositions containing these substrates to a substrate. In the establishment of adhesion, it is possible that the silanol groups that participate are primarily those that in part enter into a connection with the respective substrate, instead of condensing exclusively to each other to form organosiloxanes.

Besides the secondary amino group, the aminosilanes of formula (I) also have at least one additional, either secondary or tertiary, amino group. Said amino group can have a catalytic effect on the hydrolysis of the silane groups. Similarly, the iminosilanes of group (II) can have, besides the imino group, a secondary or tertiary amino group which can have a catalytic effect on the hydrolysis of the silane groups. In order to further accelerate the hydrolysis of the silane groups, it can be advantageous to combine an aminosilane of formula (I) or an iminosilane of formula (II) with appropriate catalysts. Suitable catalysts are particularly organotin compounds, such as dibutyltin dilaurate or dibutyltin diacetylacetonate, titanates and zirconates as well as amines, amidines, and guanidines, such as 1,4-diazabicyclo[2.2.2]octane (DABCO), diazabicyclo[5.4.0]undec-7-ene (DBU) or 1,1,3,3-tetramethylguanidine, for example.

The aminosilanes of formula (I) and/or the iminosilanes of formula (II) can be advantageously usable as adhesion promoting agents between plastics and various substrates, for coating surfaces, for example in order to improve their properties with regard to the soiling tendency, the ease of cleaning, and so forth, as an accelerator and/or as a drying agent. For this purpose, they can be used alone or as a component of solutions and compositions, for example, as a preliminary treatment agent or an activator, a first coat or primer.

Suitable substrates for the use of the aminosilanes of formula (I) or of the iminosilanes of formula (II) as adhesion promoting agent or for the coating of their surfaces are, for example, particularly the substances S1 and S2 mentioned herein.

The aminosilanes of formula (I) and the iminosilanes of formula (II) are also usable as a component of curable materials, wherein they can be used in the curable materials as crosslinking agent and/or as adhesion promoting agent and/or as accelerator and/or as drying agent, and also as a component of activators or primers.

The aminosilanes of formula (I) are novel compounds with surprising properties. They can be liquid and have a relatively low viscosity at room temperature, which can be great advantage for many applications. Nonetheless, they have a low volatility and little odor, which is often not the case with low-viscosity amino compounds. Moreover, they can be manufactured from commercial primary aminosilanes and the described aldehydes ALD of formula (IV) in a simple process which requires no expensive workup steps. This is possible since the imine formation between the tertiary aldehyde ALD and the primary amino groups occurs spontaneously without active water removal and without aminal formation, the hydrogenation, in spite of steric hindrance, succeeds surprisingly simply by way of the tertiary substituted imino group—already at a relatively low hydrogen pressure and a relatively low temperature—, and the resulting secondary amino groups of the aminosilanes of formula (I) do not participate in the alkylation reaction and thus no excess alkylation with loss of NH functionality can occur.

Besides the secondary amino group formed by hydrogenation from the imino group, the aminosilanes of formula (I) can comprise at least one additional amino group in the form of a tertiary or secondary amino group, which originates from the aldehyde ALD. Some exemplary advantageous properties of the aminosilanes of formula (I) can presumably be explained by this additional amino group, such as the properties of rapid hydrolysis rate of the silane groups, good compatibility in numerous curable materials, and particularly good adhesion promoting properties. The presence of a morpholino group for example appears to have an accelerating effect on the hydrolysis rate.

Exemplary advantageous properties are exhibited by the aminosilanes of formula (I) in adducted form, as a curable, silane crosslinking polymer. Such polymers can be prepared by reacting isocyanate functional polyurethane polymers with aminosilanes. If aminosilanes of formula (I) are used for that purpose, then silane functional polymers having a relatively low viscosity are produced, which cure rapidly and completely when they come in contact with moisture. However, it is particularly surprising that curable materials containing silane functional polymers which are derived from the aminosilanes of formula (I) can be an excellent thermal resistance in the cured state. The thermal resistance of these systems is here substantially better than the thermal resistance of similar systems derived from previously known secondary amino group-comprising aminosilanes.

The iminosilanes of formula (II) are also novel compounds with surprising properties. They can be liquid and have a relatively low viscosity at room temperature, and they can have a low volatility and little odor. Under exclusion of humidity, they are stable when stored. When they come in contact with water, hydrolysis of both the imino groups and also the silane groups occurs. The imino groups react during the hydrolysis formally to produce amino groups, wherein the corresponding aldehyde ALD is released. In the presence of groups that are reactive with respect to amines, such as isocyanate groups, for example, the primary amino groups continue to react, for example, with formation of urea groups. As a result, the hydrolysis of the imino groups occurs rapidly and completely. The released aldehyde ALD has no odor or only a slight, amine-like odor. It also does not cause the formation of an odor, or at most it causes only the formation of a slight odor, in a composition, such as an adhesive, a sealant or a covering, for example. The reaction of components that are reactive with respect to primary amines with the hydrolyzing iminosilane of formula (II) does not have to occur necessarily via the released aminosilane AS of formula (III). Naturally, reactions with intermediates of the hydrolysis of the iminosilane to form the aminosilane are also possible. For example, it is possible that the hydrolyzing iminosilane of formula (II) reacts in the form of a semiaminal directly with components that are reactive with respect to amines.

Among the described iminosilanes of formula (II), exemplary iminosilanes of formula (II a) are particularly interesting:

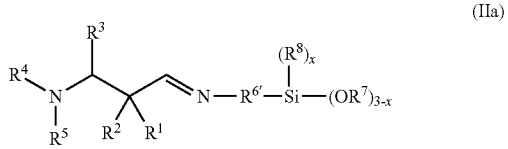

(IIa)

In the formula (IIa),

R[6'] stands, for example, for a linear alkylene residue having 5-7 C atoms, which has one or 2 secondary amino groups in the chain, such as for a —$(CH_2)_2$—NH—$(CH_2)_3$— or a —$(CH_2)_2$—NH—$(CH_2)_2$—NH—$(CH_2)_3$— residue, and $R^1$, $R^2$, $R^3$, $R^4$, $R^5$, $R^7$, $R^8$ and x have the already mentioned definitions.

The special aminosilanes AS comprising both primary and secondary amino groups, which are the basis of the iminosilanes of formula (IIa), can be particularly advantageous as adhesion promoting agents, wherein, however, their primary amine groups can lead to problems during storage in compositions, such as in compositions having ester groups. This issue can be overcome elegantly by, for example, using the iminosilanes of formula (II a) as adhesion promoting agents.

Exemplary subject matter of the present disclosure also includes an adduct AD from the reaction of at least one aminosilane of formula (I) with at least one compound VB which carries at least one, preferably for example at least two reactive groups RG, wherein the reactive groups RG are selected from the group comprising (e.g., consisting of) isocyanate, isothiocyanate, cyclocarbonate, epoxide, episulfide, aziridine, acryl, methacryl, 1-ethinylcarbonyl, 1-propinylcarbonyl, maleimide, citraconimide, vinyl, isopropenyl and allyl groups. It is preferable to use isocyanate, epoxide, acryl, maleimide, vinyl, isopropenyl and allyl groups. The isocyanate group and the epoxide group are for example, particularly preferred as reactive group RG.

At least one secondary amino group of an aminosilane of formula (I) here reacts in an addition reaction with at least one reactive group RG of the compound VB to form an adduct AD.

The reaction can be carried out in such a manner that the secondary amino groups of the aminosilane of formula (I) are present in stoichiometric amount or in a stoichiometric excess with respect to the reactive groups RG of the compound VB, wherein the adducts AD can be obtained with at least one, preferably for example with at least two silane groups, which are largely free of reactive groups RG.

However, the reaction can also be carried out in such a manner that the reactive groups RG of the compound VB are present in a stoichiometric excess with respect to the secondary amino groups of the aminosilane of formula (I). In the case where the compound VB has at least two reactive groups RG, it is possible in this manner to obtain adducts AD having at least one reactive group RG and at least one silane group.

The reaction between the aminosilane of formula (I) and the compound VB to form an adduct AD occurs under the mentioned conditions, as they can be used for reactions between the reactive groups RG that participate in the given reaction. The reaction occurs using a solvent and preferably for example in a solvent-free manner. Optionally, auxiliary agents, such as catalysts, initiators or stabilizers, for example, can also be used. The reaction with isocyanate groups is carried out preferably for example at room temperature, and the reaction with epoxide groups preferably for example at an increased temperature, for example, at 40-100° C.

Examples of suitable compounds VB are:

monomer and/or oligomer aliphatic, cycloaliphatic, arylaliphatic or aromatic polyisocyanates, such as 1,4-tetramethylene diisocyanate, 1,6-hexamethylene diisocyanate (HDI), 2-methylpentamethylene-1,5-diisocyanate, 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, and any mixtures of said isomers, 1-methyl-2,4- and -2,6-diisocyanatocyclohexane and any mixtures of said isomers (HTDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl)cyclohexane, m- and p-xylylene diisocyanate (m- and p-XDI), 1,3,5-tris-(isocyanatomethyl)benzene, m- and p-tetramethyl-1,3- and -1,4-xylylene diisocyanate (m- and p-TMXDI), bis-(1-isocyanato-1-methylethyl)naphthalene, dimer and trimer fatty acid isocyanates, such as 3,6-bis-(9-isocyanatononyl)-4,5-di-(1-heptenyl)cyclohexene (dimeryl diisocyanate), α,α,α',α',α'',α''-hexamethyl-1,3,5-mesitylene triisocyanate, 2,4- and 2,6-toluylene diisocyanate and any mixtures of said isomers (TDI), 4,4'-, 2,4'- and 2,2'-diphenyl methane diisocyanate and any mixtures of said isomers (MDI), mixtures of MDI and MDI homologs (polymer MDI or PMDI), 1,3- and 1,4-phenylene diisocyanate, 2,3,5,6-tetramethyl-1,4-diisocyanatobenzene, naphthalene-1,5-diisocyanate (NDI), 3,3'-dimethyl-4,4'-diisocyanatodiphenyl (TODD, dianisidine diisocyanate (DADI), tris-(4-isocyanatophenyl)methane, tris-(4-isocyanatophenyl)thiophosphate; oligomers of said isocyanates containing uretdione, isocyanurate or iminooxadiazindione groups; modified polyisocyanates containing ester, urea, urethane, biuret, allophanate, carbodiimide, uretonimine or oxadiazintrione groups; as well as polyurethane polymers containing isocyanate groups, that is to say more-than-one-isocyanate-containing reaction products of polyisocyanates with substances that contain two or more hydroxyl groups (so-called "polyols"), such as, for example, polyvalent alcohols, glycols or amino alcohols, polyhydroxy functional polyethers, polyesters, polyacrylates, polycarbonates or polyhydrocarbons, such as polyethers, as mentioned below for the manufacture of polyurethane polymers PUP comprising isocyanate groups;

polyepoxides, such as bis-(2,3-epoxycyclopentyl)ether, polyglycidyl ethers of polyvalent, aliphatic and cycloaliphatic alcohols, such as 1,4-butanediol, polypropylene glycols and 2,2-bis-(4-hydroxycyclohexyl)propane; polyglycidyl ethers of polyvalent phenols, such as resorcinol, bis-(4-hydroxyphenyl)methane (bisphenol F), 2,2-bis-(4-hydroxyphenyl)propane (bisphenol A), 2,2-bis-(4-hydroxy-3,5-dibromophenyl)propane, 1,1,2,2-tetrakis-(4-hydroxyphenyl)ethane, condensation products of phenols with formaldehyde, which were prepared under acidic conditions, such as phenol novolaks, and cresol novolaks, as well as with these alcohols and phenols, or with polycarboxylic acids, such as, dimeric acids, for example, or a mixture thereof, previously lengthened polyglycidyl ethers; polyglycidyl esters of polyvalent carboxylic acids, such as phthalic acid, terephthalic acid, tetrahydrophthalic acid, and hexahydrophthalic acid; N-glycidyl derivatives of amines, amides and heterocyclic nitrogen bases, such as N,N-diglycidylaniline, N,N-diglycidyltoluidine, N,N,O-triglycidyl-4-aminophenol, N,N,N',N'-tetraglycidyl-bis-(4-aminophenyl)methane, triglycidyl cyanurate, and triglycidyl isocyanurate;

compounds that carry more than one acryl, methacryl or acrylamide group, such as tris-(2-hydroxyethyl)isocyanurate-tri(meth)acrylate, tris-(2-hydroxyethyl)cyanurate-tri(meth)acrylate, N,N',N''-tris-(meth)acryloylperhydrotriazine; acrylates and methacrylates of aliphatic polyethers, polyesters, novolaks, phenols, and aliphatic or cycloaliphatic alcohols, glycols and polyester glycols as well as mono- and polyalkoxylated derivatives of the above-mentioned compounds, for example, ethylene glycol di(meth)acrylate, tetraethylene glycol di(meth)acrylate, tripropylene glycol di(meth)acrylate, polyethylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, trimethylolpropane tri(meth)acrylate, pentaerythritol tetra(meth)acrylate, dipentaerythritol tetra(meth)acrylate, dipentaerythritol penta(meth)acrylate, dipentaerythritol hexa(meth)acrylate; acryl or methacryl functional polybutadienes, polyisoprenes or block copolymers thereof; adducts of polyepoxides, such as the above-mentioned epoxides with acrylic and methacrylic acid; polyurethane(meth)acrylates; acrylamides, such as N,N'-methylene-bis-acrylamide;

compounds carrying more than one 1-ethinylcarbonyl or 1-propinylcarbonyl group;

compounds carrying more than one maleimide or citraconimide group;

compounds carrying more than one vinyl and/or isopropenyl group;

compounds carrying more than one allyl group;

as well as heterofunctional compounds, that is to say compounds that carry at least two different of the above-mentioned reactive groups, as well as compounds that are monofunctional with respect to the reactive groups RG, in particular those compounds that additionally carry a silane group, such as, in particular, isocyanatosilanes, epoxysilanes and (meth)acrylsilanes, particularly 3-isocyanatopropyltrimethoxysilane and 3-glycidoxypropyltrimethoxysilane.

During the—at least partial—hydrolysis of the adducts AD, compounds with silanol groups of formula (IX) form, as already described for aminosilanes of formula (I) and iminosilanes of formula (II).

Such hydrolyzed or partially hydrolyzed adducts AD with silanol groups of formula (IX) are highly reactive and they are capable of continuing to react very rapidly, in the same manner as already described herein.

Particularly suitable as compound VB are, in an exemplary embodiment, monomer and oligomer polyisocyanates, isocyanatosilanes, polyepoxides, epoxysilanes and compounds having (meth)acryl groups.

Adducts AD with such compounds VB are, for example, particularly suited as a component of curable materials, wherein they can act in the curable materials as crosslinking agent and/or as adhesion promoting agent and/or as accelerator and/or as drying agent, and as a component of activators or primers.

Particularly suitable as compound VB are, in additional exemplary embodiments, reaction products—having more than one isocyanate group—from reacting polyisocyanates with polyols (also referred to as isocyanate group-containing polyurethane polymers).

Adducts AD with such compounds VB are, for example, particularly suitable as a component of curable materials, wherein they can be used in the curable materials as curable, silane functional polymer.

The aminosilanes of formula (I) and also the iminosilanes of formula (II) and the adducts AD are for example advantageously usable as adhesion promoting agent and/or accelerator and/or drying agent, for coating surfaces or as a component of curable materials, activators or primers.

A further subject matter of the present disclosure encompasses compositions containing at least one aminosilane of formula (I) and/or one iminosilane of formula (II) and/or at least one adduct AD.

In an exemplary embodiment, such a composition is an activator which additionally contains at least one solvent, and optionally additional components, such as, in particular, catalysts, additional silanes, titanates and zirconates. An activator can be used to clean substrate surfaces and prepare them at the same time for the subsequent application of a curable material, in such a manner that an improved adhesion between substrate and composition is produced. The ingredients in an activator are for example dosed in such a manner that, after the evaporation of the solvent, no closed film remains on the substrate surface.

In a further exemplary embodiment, such a composition is a primer which contains additionally at least one solvent and at least one film forming component, as well as optionally additional components, such as, in particular, catalysts, fillers, additional silanes, titanates, zirconates, crosslinking agents and additional additives. Particularly suitable film forming components are monomer and/or oligomer aliphatic, cycloaliphatic, arylaliphatic or aromatic polyisocyanates, isocyanate- and/or silane group-containing polyurethane polymers, epoxide resins as well as the described adducts AD. The primer can be applied in such a manner that, after the evaporation of the solvent, a closed film in a layer thickness in the range from several micrometers to several hundredths of micrometers remains on the substrate. A primer can be used to improve the adhesion between substrate and composition, by making it possible for the primer film, as well as the curable material, to build up adhesion to the substrate and also to a curable material applied to the primer film.

Suitable solvents for such activators or primers are, for example, alcohols, such as methanol, ethanol, isopropanol; ketones, such as acetone, methyl ethyl ketone, diisobutyl ketone, acetylacetone, mesityl oxide, cyclohexanone, methylcylcohexanone; acetates, such as ethyl acetate, propyl acetate, butyl acetate; formiates, propionates and malonates, such as diethylmalonate; ethers, such as dialkyl ethers, ketone ethers and ester ethers, for example, diisopropyl ether, diethyl ether, dibutyl ether, diethylene glycol diethyl ether and ethylene glycol diethyl ether; aliphatic and aromatic hydrocarbons, such as toluene, xylene, heptane, octane, and mineral oil fractions, such as naphtha, white spirit, petroleum ether and gasoline, for example, Solvesso™ types (from Exxon); halogenated hydrocarbons, such as methylene chloride; carbonates, such as, for example, propylene carbonate; lactones, such as, for example, butyrolactone; N-alkylated lactams, such as, for example, N-methylpyrrolidone; as well as water.

In a further embodiment, such a composition is a curable material in the form of an isocyanate group-containing polyurethane composition, or in the form of an epoxide resin composition, or in the form of a silane functional curable material, which cures primarily via the hydrolysis and condensation of silane groups.

Such curable materials can be used, for example, as casting compounds, sealants, adhesives, coverings, coatings and paints for building and industry applications, for example, as electrical insulation materials, putty compositions, joint sealants, assembly adhesives, car body adhesives, glass adhesives, sandwich element adhesives, cladding adhesives, laminating adhesives, anchoring adhesives, floor coatings and coverings, balcony and roof coverings, concrete protection coverings, parking garage coverings as well as protective paints against corrosion.

The use of silanes in curable materials, activators and primers is known, wherein the silanes can be used as crosslinking agent and/or as adhesive and/or as accelerator and/or as drying agent and/or as curable polymer. The fact that the aminosilanes of formula (I) have an additional amino group can make them particularly advantageous for such applications.

Among the described adducts AD, silane functional polymers SP that can be particularly advantageous include those that can be prepared by reacting at least one isocyanate group-containing polyurethane polymer PUP with at least one aminosilane of formula (I).

For this purpose, it is for example preferred to use aminosilanes of formula (I) having only one secondary group, that is aminosilanes of formula (I) in which $R^5$ does not stand for a hydrogen atom and in which $R^6$ has no secondary amino groups.

The secondary amino groups of the aminosilanes of formula (I) can for example, be used preferably in stoichiometric amount or in a slight stoichiometric excess with respect to the isocyanate groups of the polyurethane polymers PUP.

It is preferred for example, to use silane functional polymers SP which are free of isocyanate groups.

A polyurethane polymer PUP comprising isocyanate groups that is suitable for the manufacture of a silane functional polymer SP can be prepared, for example, by reacting at least one polyol with at least one polyisocyanate, such as a diisocyanate. This reaction can take place by reacting the polyol and the polyisocyanate using the known methods, for example, at exemplary temperatures from 50° C. to 100° C., optionally with the simultaneous use of suitable catalysts, wherein the polyisocyanate is dosed in such a manner that the isocyanate groups thereof are present in stoichiometric excess with respect to the hydroxyl groups of the polyol. Advantageously, the polyisocyanate can be dosed in such a manner that an exemplary NCO/OH ratio of 1.3-5, for example 1.5-3, is maintained. The term "NCO/OH ratio" denotes the ratio of the number of isocyanate groups used to the number of hydroxyl groups used. It is preferable for example that, after the reaction of all the hydroxyl groups of the polyol, a content of free isocyanate groups of 0.25-5 wt %, particularly preferably 0.3-2.5 wt %, remains in the polyurethane polymer PUP.

Optionally, the polyurethane polymer PUP can be manufactured with the simultaneous use of plasticisers, wherein the plasticisers used contain no groups that are reactive with respect to isocyanates.

It is preferred for example to use polyurethane polymer PUP having the mentioned content of free isocyanate groups, which are obtained by reacting diisocyanates with high molecular weight diols in an NCO/OH ratio of 1.5-2.

As polyols for the manufacture of a polyurethane polymer PUP, it is possible to use, for example, the following commercial polyols or mixtures thereof:

polyoxyalkylene polyols, also referred to as polyether polyols or oligoetherols, which are polymerization products of ethylene oxide, 1,2-propylene oxide, 1,2- or 2,3-butylene oxide, oxetane, tetrahydrofuran or mixtures thereof, possibly polymerized with the help of a starter molecule with two or more active hydrogen atoms, such as, for example, water, ammonia or compounds having several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, as well as mixtures of the mentioned compounds. It is possible to use both polyoxyalkylene polyols that have a low degree of unsaturation (measured according to ASTM D-2849-69 and indicated in milliequivalent unsaturation per gram polyol (mEq/g)), manufactured, for example, with the help of so-called double metal cyanide complex catalysts (DMC catalysts), and also polyoxyalkylene polyols with a higher degree of unsaturation, manufactured, for example, with the help of anionic catalysts, such as NaOH, KOH, CsOH or alkali alcoholates.

Particularly suitable are for example polyoxyalkylene diols or polyoxyalkylene triols, such as polyoxyethylene and polyoxypropylene diols and triols. Particularly suitable are for example polyoxyalkylenediols and triols having a degree of unsaturation of less than 0.02 mEq/g and a molecular weight in the range of 1000-30,000 g/mol, as well as polyoxypropylene diols and triols having a molecular weight of 400-8000 g/mol.

Also particularly suitable are for example so-called ethylene oxide end capped ("EO endcapped") polyoxypropylene polyols. The latter are special polyoxypropylene polyoxyethylene polyols prepared, for example, by the further alkoxylation of pure polyoxypropylene polyols, particularly polyoxypropylene diols and triols, after the end of the polypropoxylation reaction with ethylene oxide, and as a result they contain primary hydroxyl groups.

Styrene-acrylonitrile or acrylonitrile-methyl methacrylate grafted polyether polyols.

Polyester polyols, also referred to as oligoesterols, manufactured by known methods, particularly the polycondensation of hydroxycarboxylic acids, or the polycondensation of aliphatic and/or aromatic polycarboxylic acids with bivalent or polyvalent alcohols.

Polyester polyols that are particularly suitable are those that are manufactured from bivalent to trivalent, including bivalent alcohols, such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimerdiol), hydroxypivalic acid neopentyl glycol esters, glycerol, 1,1,1-trimethylolpropane or mixtures of the above-mentioned alcohols, with organic di- or tricarboxylic acids, particularly dicarboxylic acids, or their anhydrides or esters, such as, for example, succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl terephthalate, hexahydrophthalic acid, trimellitic acid and trimellitic acid anhydride, or mixtures of the above-mentioned acids, as well as polyester polyols from lactones, such as, for example, from c-caprolactone, and starters, such as the above-mentioned bivalent or trivalent alcohols.

Polyester diols are for example particularly suitable polyester polyols.

Polycarbonate polyols, such as those that can be prepared by reacting, for example, the above-mentioned alcohols—used for building up the polyester polyols—with dialkyl carbonates, diaryl carbonates or phosgene.

Block copolymers carrying at least two hydroxyl groups and comprising at least two different blocks having a polyether, polyester and/or polycarbonate structure of the above-mentioned type, such as polyether polyester polyols.

Polyacrylates and polymethacrylate polyols.

Polyhydroxy functional fats and oils, for example, natural fats and oils, particularly castor bean oil; or—so-called oleochemical—polyols prepared by chemically modifying natural fats and oils, for example, the epoxy polyesters or epoxy polyethers obtained by epoxidizing unsaturated oils, followed by ring opening with carboxylic acids or alcohols, or polyols obtained by hydroformylation and hydrogenation of unsaturated oils; or from natural fats or oils by degradation processes, such as alcoholysis or ozonolysis, and subsequent chemical linking, for example, by the transesterifcation or dimerization of the resulting degradation products or derivatives of resulting polyols. Suitable degradation products of natural fats and oils are for example particularly fatty acids and fatty alcohols as well as fatty acid esters, such as the methyl esters (FAME), which can be derivatized, for example, by hydroformylation and hydrogenation to form hydroxy fatty acid esters.

Polyhydrocarbon polyols, also referred to as oligohydrocarbonols, such as, in particular, polyhydroxy functional polyolefins, polyisobutylenes, polyisoprenes; polyhydroxy functional ethylene-propylene, ethylene-butylene or ethylene-propylene-diene copolymers, as manufactured, for example, by the company Kraton Polymers; polyhydroxy functional polymers of dienes, in particular of 1,3-butadiene, which can also be manufactured particularly by anionic polymerization; polyhydroxy functional copolymers from dienes, such as 1,3-butadiene or diene mixtures, and vinyl monomers, such as styrene, acrylonitrile, vinyl chloride, vinyl acetate, vinyl alcohol, isobutylene and isoprene, for example, polyhydroxy functional acrylonitrile/butadiene copolymers, such as those that can be manufactured from epoxides or amino alcohols and carboxyl end capped acrylonitrile/butadiene copolymers (available commercially, for example, under the name Hypro® (formally Hycar®), CTBN and CTBNX and ETBN from Nanoresins AG, Germany, or Emerald Performance Materials LLC); as well as hydrogenated polyhydroxy functional polymers or copolymers of dienes.

These mentioned polyols preferably have an exemplary mean molecular weight of 250-30,000 g/mol, in particular 1000-30,000 g/mol, and they preferably have an exemplary mean OH functionality in the range of 1.6-3.

Exemplary preferred polyols are polyether, polyester, polycarbonate and polyacrylate polyols, preferably diols and triols. It can be particularly preferred to use, for example, polyether diols, such as polyoxypropylene and polyoxypropylenepolyoxyethene diols. It is most preferable to use, for example, high molecular weight polyoxypropylene diols having an exemplary degree of unsaturation of less than 0.02 mEq/g and an exemplary molecular weight in the range of 4000-30,000 g/mol, in particular 8000-30,000 g/mol.

In addition to these mentioned polyols, small quantities of low molecular weight bivalent or polyvalent alcohols, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimer fatty alcohols, 1,1,1-trimethylolethane, 1,1,1-trimethylolpropane, glycerol, pentaerythritol, sugar alcohols, such as xylitol, sorbitol or mannitol, sugars, such as sucrose, other higher valence alcohols, low molecular weight alkoxylation products of the above-mentioned bivalent and polyvalent alcohols, as well as mixtures of the above-mentioned alcohols can be used at the same time in the manufacture of a polyurethane polymer PUP. Similarly, small quantities of polyols having a mean OH functionality of more than 3 can also be used at the same time, for example, sugar polyols.

As polyisocyanate for the manufacture of a polyurethane polymer PUP which comprises isocyanate groups, aromatic or aliphatic polyisocyanates, such as diisocyanates, are used.

Particularly suitable exemplary aromatic polyisocyanates are the monomeric di- or triisocyanates, such as 2,4- and 2,6-toluylene diisocyanate and any mixtures of said isomers (TDI), 4,4'-, 2,4'- and 2,2'-diphenylmethane diisocyanate and any mixtures of said isomers (MDI), mixtures of MDI and MDI homologs (polymer MDI or PMDI), 1,3- and 1,4-phenylene diisocyanate, 2,3,5,6-tetramethyl-1,4-diisocyanatobenzene, naphthalene-1,5-diisocyanate (NDI), 3,3'-dimethyl-4,4'-diisocyanatodiphenyl (TODD, dianisidine diisocyanate (DADI), tris-(4-isocyanatophenyl)methane, tris-(4-isocyanatophenyl)thiophosphate, as well as any mixtures of the above-mentioned isocyanates. MDI and TDI are for example preferred.

Aliphatic polyisocyanates that are particularly suitable include the monomeric di- or triisocyanates, such as 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane and any mixtures of said isomers (HTDI or $H_6$TDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or $H_{12}$MDI), 1,4-diisocyanato-2,2,6-trimethylcyclohexane (TMCDI), 1,3- and 1,4-bis-(isocyanatomethyl)cyclohexane, m- and p-xylylene diisocyanate (m- and p-XDI), m- and p-tetramethyl-1,3- and -1,4-xylylene diisocyanate (m- and p-TMXDI), 1,3,5-tris-(isocyanatomethyl)benzene, bis-(1-isocyanato-1-methylethyl)naphthalene, dimer and trimer fatty acid isocyanates, such as 3,6-bis-(9-isocyanatononyl)-4,5-di-(1-heptenyl)cyclohexene (dimeryl diisocyanate), $\alpha,\alpha,\alpha',\alpha',\alpha'',\alpha''$-hexamethyl-1,3,5-mesitylene triisocyanate, as well as any mixtures of the above-mentioned isocyanates. HDI and IPDI are preferred.

An exemplary silane functional polymer SP has end capping groups of formula (X):

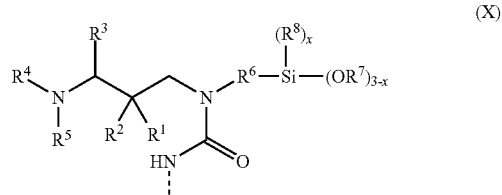

In the formula (X), $R^1$, $R^2$, $R^3$, $R^4$, $R^5$, $R^6$, $R^7$, $R^8$ and x have the already mentioned definitions.

A silane functional polymer SP can be stored with exclusion of moisture. In contact with moisture, the silane groups of the polymer SP hydrolyze, and after that the polymer cures to a crosslinked plastic. Thus, the present disclosure also describes a crosslinked plastic which was obtained by reacting at least one silane functional polymer SP with moisture.

A silane functional polymer SP can have various exemplary advantageous properties. It can be prepared in a simple manner from the described aminosilanes of formula (I), and it has little odor, even in the case of an excess of aminosilane. Its viscosity is relatively low, and clearly lower than that of a corresponding silane functional polymer prepared using a primary aminosilane. In the case of contact with moisture, it crosslinks rapidly and completely to a cured polymer having excellent properties, in particular a good resilience with high strength and high ductility, and a surprisingly good thermal resistance, for example, at a thermal load of 90° C. The thermal resistance is clearly superior to that of cured silane functional polymers which were manufactured using previously known secondary aminosilanes.

A silane functional polymer SP is for example, particularly well suitable as a component of curable materials, such as for the formulation of silane functional, moisture curing compositions.

A further subject matter of the present disclosure encompasses an exemplary moisture curing composition which contains at least one silane functional polymer SP, as described herein, and at least one additional component.

The silane functional copolymer SP can be present in an exemplary quantity of 10-80 wt %, such as preferably in a quantity of 15-50 wt %, relative to the moisture curing composition.

As additional components, one can use, among other substances, the following auxiliary substances and additives:

Silanes, which can act as adhesion promoting agents, crosslinking agents, drying agents and/or catalysts, such as, in particular, additional aminosilanes, in particular the described aminosilanes of formula (I), the aminosilanes AS mentioned for their manufacture that have primary amino groups or additional aminosilanes having secondary or tertiary amino groups, and in particular N-phenyl, N-cyclohexyl and N-alkylaminosilanes, moreover mercaptosilanes, epoxysilanes, vinylsilanes, (meth)acrylsilanes, isocyanatosilanes, carbamatosilanes, alkylsilanes, S-(alkylcarbonyl)mercaptosilanes, and iminosilanes, as well as oligomer forms of said silanes, particularly 3-glycidoxypropyltrimethoxysilane, 3-aminopropyltrimethoxysilane, N-(2-aminoethyl)-3-aminopropyltrimethoxysilane, N-(2-aminoethyl)-N═-[3-(trimethoxysilyl)propyl]ethylenediamine, 3-mercaptopropyltrimethoxysilane, 3-isocyanatopropyltrimethoxysilane, 3-ureidopropyltrimethoxysilane, 3-chloropropyltrimethoxysilane, vinyltrimethoxysilane, or the corresponding organosilanes with ethoxy groups instead of the methoxy groups, as well as oligomer forms of said silanes;

plasticisers, particularly carboxylic acid esters, such as phthalates, particularly dioctyl phthalate, diisononyl phthalate or diisodecyl phthalate, adipates, particularly dioctyl adipate, azelates, sebacates, polyols, particularly polyoxyalkylene polyols or polyester polyols, glycol ethers, glycol esters, organic phosphoric and sulfonic acid esters or polybutenes;

Reactive diluents and crosslinking agents, for example, silane functional oligomers and polymers, natural resins, fats or oils, such as colophony, shellac, linseed oil, castor bean oil and soybean oil;

Nonreactive thermoplastic polymers, such as, for example, homopolymers or copolymers of unsaturated monomers, particularly from the group comprising ethylene, propylene, butylene, isobutylene, isoprene, vinyl acetate and alkyl(meth)acrylates, particularly polyethylenes (PE), polypropylenes (PP), polyisobutylenes, ethylene-vinyl acetate copolymers (EVA), and atactic poly-α-olefins (APAO);

Solvents;

Inorganic and organic fillers, such as ground or precipitated calcium carbonates which are optionally coated with fatty acids, particularly stearates; barite (heavy spar), talcs, quartz meals, quartz sand, dolomites, wollastonites, kaolins, calcined kaolins, mica (potassium-aluminum silicate), molecular sieves, aluminum oxides, aluminum hydroxides, magnesium hydroxide, silicic acids including highly dispersed silicic acids from pyrolysis processes, soots including industrially manufactured soots, graphite, metal powders, such as aluminum, copper, iron, silver or steel, PVC powders or hollow beads;

Fibers, particularly glass fibers, carbon fibers, metal fibers, ceramic fibers or plastic fibers, such as polyamide fibers or polyethylene fibers;

Pigments, for example, titanium oxide or iron oxides;

Catalysts, such as organotin compounds, such as, in particular, dibutyltin dichloride, dibutyltin oxide, dibutyltin diacetate, dibutyl dilaurate, dibutyltin diacetylacetonate, additional dibutyltin dicarboxylates, dioctyltin dicarboxylates, such as, in particular, dioctyltin dilaurate, monobutyltin trichloride, tin(II)-octoate, alkyltin thioesters, moreover compounds of zinc, manganese, iron, chromium, cobalt, copper, nickel, molybdenum, lead, cadmium, mercury, antimony, vanadium, titanium, zirconium or potassium, as well as further amines, amidines and guanidines, particularly N-ethyldiisopropylamine, N,N,N',N'-tetramethylalkylenediamines, bis-(N,N-diethylaminoethyl)adipate, tris-(3-dimethylaminopropyl)amine, 1,4-diazabicyclo[2.2.2]octane (DABCO), 1,8-diazabicyclo[5.4.0]undec-7-ene (DBU), 1,5-diazabicyclo[4.3.0]non-5-ene (DBN), N,N'-dimethylpiperazine, 1,1,3,3-tetramethylguanidine, nitrogen aromatic compounds, such as 4-dimethylaminopyridine, N-methylimidazole, N-vinylimidazole or 1,2-dimethylimidazole; organic ammonium compounds or alkoxylated tertiary amines; as well as furthermore combinations of the mentioned compounds, such as combinations of different metal compounds or combinations of metal compounds and nitrogen-containing compounds.

Rheology modifiers, such as, in particular, thickeners, for example, layer silicates, such as bentonites, derivatives of castor bean oil, hydrogenated castor bean oil, polyamides, polyurethanes, urea compounds, pyrogenic silicic acids, cellulose ethers, and hydrophobically modified polyoxyethylenes;

Drying agents, such as, in particular, tetraethoxysilane, vinyltrimethoxysilane, and organoalkoxysilanes which have a functional group in a position relative to the silane group, in particular N-(methyldimethoxysilylmethyl)-O-methylcarbamate, (methacryloxymethyl)silanes, methoxymethylsilanes, orthoformic acid ester, calcium oxide or molecular sieves;

Stabilizers against oxidation, heat, light and UV radiation;

Fire retardants, such as the already mentioned fillers aluminum hydroxide and magnesium hydroxide, as well as, for example, organic phosphoric acid esters, such as, in particular, triethyl phosphate, tricresyl phosphate, triphenyl phosphate, diphenyl cresyl phosphate, isodecyldiphenyl phosphate, tris(1,3-dichloro-2-propyl)phosphate, tris(2-chloroethyl)phosphate, tris(2-ethylhexyl)phosphate, tris (chloroisopropyl)phosphate, tris-(chloropropyl)phosphate, isopropylated triphenyl phosphate, mono-, bis- and tris(isopropylphenyl)phosphates having various degrees of isopropylation, resorcinol-bis(diphenyl phosphate), bisphenol A bis (diphenyl phosphate), and ammonium polyphosphates;

surface-active substances, such as, in particular, crosslinking agents, leveling agents, aeration agents or defoaming agents;

biocides, such as, for example, algicides, fungicides or fungal growth inhibiting substances;

as well as additional substances that are usually used in moisture curing compositions.

It can be advantageous to ensure that the additional components do not affect the storage stability of the moisture curing composition, that is, during the storage, they should not trigger to a significant extent the reaction of the silane groups contained in the composition, reaction which leads to crosslinking. This can mean that such additional exemplary components preferably contain no water or at most traces of water. It can be appropriate to chemical or physically dry certain components prior to mixing into the composition.

The moisture curing composition can, for example, preferably contain plasticisers, fillers, silanes and/or catalysts.

The moisture curing composition can be stored for a time period of several months to one year and longer, with exclusion of moisture, in an appropriate packaging or arrangement, such as a barrel, a pouch or a cartridge, for example, without the composition undergoing a change in its usage properties, or in its properties after curing, to an extent relevant to its use. The storage stability can be determined by measuring the viscosity, the push-out quantity or the push-out force.

An exemplary composition preferably contains no free isocyanate groups. Such an isocyanate-free composition can be advantageous from the toxicological point of view.

The moisture curing composition can be in the form of a single-component composition or in the form of a two-component composition.

The term "single-component" in the present document denotes for example a curable composition wherein all the components of the composition are stored mixed in the same container, which composition is storage stable at room temperature for a time period ranging from several weeks to months—and thus it undergoes no or only insubstantial changes in its usage or use properties due to the storage—and which is curable with moisture.

The term "two-component" in the present document denotes for example, a composition in which the ingredients of the composition are present in two different components which are stored in mutually separate containers and which are each individually storage stable at room temperature. It is only shortly before or during the application of the composition that the two components are mixed with each other, and after this the mixed composition cures completely, wherein the curing occurs only due to the action of the moisture.

In the case of the application of the moisture curing composition to at least one solid or article, the silane groups of the polymer and optionally present additional silanes come in contact with moisture. The silane groups have the property of hydrolyzing when they come in contact with moisture. In the process, organosilanols (silicon organic compounds containing one or more silanol groups, Si—OH groups) form, and, as a result of subsequent condensation reactions, organosiloxanes (silicon organic compounds containing one or more siloxane groups, Si—O—Si groups) form. As a result of these reactions, which can be accelerated by using catalysts, the composition finally cures completely; this process is also referred to as crosslinking. Moreover, silanol groups can condense, for example, with hydroxyl groups of the substrate to which the moisture curing composition is applied, as a result of which, during the curing, an excellent adhesion of the composition to the substrate can develop. The water used for the curing reaction can originate either from the air (air moisture), or, on the other hand, the composition can be brought in contact with a water-containing component, for example, by brushing on, for example, using a smoothing agent, or by spraying, or a water-containing component can be added to the composition during the application, for example, in the form of a water-containing paste which is mixed in, using a static mixer, for example.

The described moisture curing composition cures completely when it comes in contact with moisture. Thus, the present disclosure also describes a cured composition which is obtained by reacting at least one silane functional polymer SP with moisture.

The curing occurs at different rates, depending on the temperature, the type of contact, the quantity of moisture, and the presence of any catalysts. During curing by means of air moisture, a skin forms first on the surface of the composition. The so-called skin formation time accordingly represents a measure of the rate of curing the cured state, the composition has a good resilience with high strength and high ductility, and a surprisingly good thermal resistance, for example, at a thermal load of 90° C. As a result, it is suitable for numerous uses, such as a fiber composite (composite), resilient casing compound, sealant, adhesive, covering, coating or paint for building and industry applications, for example, as electrical insulation materials, putty compounds, joint sealants, assembly adhesives, car body adhesives, glass adhesives, sandwich element adhesives, cladding adhesives, laminating adhesives, anchoring adhesives, floor coatings and coverings, balcony and roof coverings, concrete protection coverings, parking garage coverings as well as protective paints against corrosion, sealing, paints, lacquer and primer.

Moreover, the composition is suitable for a use as a foamed material, such as those compositions that contain silane functional polymers SP derived from aminosilanes of formula (I) with $R^6$=methylene, which thus comprise so-called α-aminosilane groups.

Suitable uses are, for example, the gluing of components in above and in below ground level buildings, and in the manufacture or repair of industrial products or consumer products, particularly windows, household machines or transport means, such as water and land vehicles, preferably automobiles, buses, trucks, trains or ships; the sealing of joints, seams and hollow spaces in industrial manufacture or repair, or in above and in below ground level buildings; as well as the coating of various substrates, for example, as floor covering, for example, for offices, living spaces, hospitals, schools, storage facilities, and parking garages, or as a sealing of a building to be applied in liquid form, in particular as a roof film.

In an exemplary preferred embodiment, the moisture curing composition is used as a resilient adhesive or sealant.

For a use of the composition as a sealant, for example, for joints in above and in below ground level buildings, or for a use as an adhesive for resilient gluing, for example, in vehicle construction, the composition can for example preferably have a pasty consistency with structure-viscose properties. Such a pasty sealant or adhesive is applied onto the substrate by means of an appropriate device. Suitable methods of application are, for example, the application from commercial cartridges, which are operated manually or with pressurized air, or from a barrel or drum by means of a conveyance pump or an extruder, optionally by means of an application robot.

A sealant or adhesive with good application properties can have a high stability and be associated with short-length stringing. This means that, after the application, it stays in the applied form, that is it does not flow apart, and, after the application apparatus is taken away, it pulls no or only a very short thread, so that the substrate is not soiled.

An adhesive for elastic gluing, for example, in vehicle construction, is for example, preferably applied in the form of a bead having a substantially round or triangular cross-sectional surface.

When used as an adhesive, the composition can be applied onto a substrate S1 and/or a substrate S2. The adhesive can thus be applied on one or the other substrate, or on both substrates. Subsequently, the parts to be glued are joined, after which the adhesive cures due to contact with moisture. Care should be taken here to ensure that the joining of the parts occurs within the so-called open time, to ensure reliable gluing of the two joined parts to each other.

When used as a sealant, the composition can be applied between the substrates S1 and S2, and the curing of the composition occurs subsequently as a result of contact with moisture. The sealant can be pressed into a joint.

In both uses, the substrate S1 can be the same as or different from the substrate S2.

Suitable substrates S1 or S2 are for example:

Glass, glass ceramics, concrete, mortar, tiles brick, gypsum and natural stones such as granite or marble;

Metals and alloys, such as aluminum, iron, steel and non-ferrous metals, as well as surface-refined metals and alloys, such as zinc coated or chromium coated metals;

Leather, textiles, paper, wood, with resins, for example, phenol, melamine or epoxide resins, bonded wood materials, resin-textile composites and additional so-called polymer composites;

Plastics, such as polyvinyl chloride (hard and soft PVC), acrylonitrile-butadiene-styrene copolymers (ABS), polycarbonate (PC), polyamide (PA), polyester, poly(methyl methacrylate) (PMMA), polyester, epoxide resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), wherein the plastics can for example preferably be surface-treated by plasma, corona or flames;

Fiber-reinforced plastics, such as carbon fiber-reinforced plastics (CFP), glass fiber-reinforced plastics (GFP) and sheet molding compounds (SMC);

Coated substrates, such as powder coated metals or alloys; and

Paints and lacquers, particularly automobile topcoat lacquer.

If desired, the substrates can be subjected to a preliminary treatment before the application of the adhesive or sealant. Such preliminary treatments can for example, comprise particularly physical and/or chemical cleaning methods, for example, grinding, sandblasting, brushing or the like, or the treatment with cleaners or solvents, or the application of an adhesion promoting agent, an adhesion promoting solution or a primer.

After the gluing or sealing of the substrates S1 and S2 by means of a composition as disclosed herein, a glued or sealed article is obtained. Such an article can be a building, such as a building above ground level or below ground level, or a means of transport, for example, a water or land vehicle, in particular an automobile, a bus, a truck, a train or a ship, or an attachment part.

The moisture curing composition can have a relatively low base viscosity, since the silane functional polymer SP has a relatively low viscosity, which allows the setting of good application properties. The moisture curing composition rapidly cures and, in the cured state, it has good resilience with high strength and high ductility, and a surprisingly good thermal resistance, for example, at a temperature load of 90° C. In comparison to previously known systems, which contain, instead of a silane functional polymer SP, a known silane functional polymer, the thermal resistance in the cured state as disclosed herein is clearly better.

EXAMPLES

1. Description of the Measurement Methods

The amine content, that is to say the total content of free amino groups and blocked amino groups (aldimino groups) in the manufactured compounds, was determined by titrimetry (with 0.1 N $HClO_4$ in acetic acid, against crystal violet) and it is indicated in mmol N/g.

Infrared spectra were measured as undiluted films on a Perkin-Elmer FT-IR 1600 apparatus provided with a horizontal ATR measurement unit with ZnSe crystal; the absorption bands are indicated in wave numbers ($cm^{-1}$) (measurement window: 4000-650 $cm^{-1}$); the addition sh indicates a band that appears as a shoulder.

$^1$H-NMR spectra were measured on a Bruker DPX-300 spectrometer at 300.13 MHz; the chemical shifts δ are indicated in ppm relative to tetramethylsilane (TMS), coupling constants J are indicated in Hz. True and pseudo coupling patterns are not differentiated.

The viscosities were measured on a cone plate viscosimeter Rheotec RC30 (cone diameter 50 mm, cone angle 1°, cone apex-plate separation 0.05 mm, shearing rate 10-100 $s^{-1}$).

2. Manufacture of Aldehydes of Formula (IV)

2,2-Dimethyl-3-(N-morpholino)propanal

Under a nitrogen atmosphere, 83.1 g (1.00 mol) 36% aqueous formaldehyde and 75.0 g (1.04 mol) isobutyraldehyde are placed in a round-bottom flask. Under thorough stirring and ice cooling, 87.1 g (1.00 mol) morpholine are slowly added using a dripping funnel, making sure that the temperature of the reaction mixture does not exceed 20° C. After the addition has been completed, the preparation was stirred for one hour at room temperature. The resulting reaction mixture was stirred in the oil bath at 100° C. for 18 hours at reflux, then cooled to room temperature, and the phases were separated in the separation funnel. The organic phase was fractionated in a vacuum without further processing. The product distilled at a head temperature of 97° C. and at a pressure of 14 mbar.

2,2-Dimethyl-3-dimethylaminopropanal

In the same manner as described for 2,2-dimethyl-3-(N-morpholino)propanal, 83.1 g (1.00 mol) 36% aqueous formaldehyde, 79.3 g (1.10 mol) isobutyraldehyde and 112.7 g (1.00 mol) 40% aqueous dimethylamine were reacted with each other. During the purification, the product distilled at a head temperature of 94° C. and at a pressure of 16 mbar.

3. Manufacture of Iminosilanes of Formula (II)

General Manufacturing Procedure (Iminosilanes)

An aldehyde was placed into a round-bottom flask under a nitrogen atmosphere, 2-propanamine was added dropwise, the preparation was stirred for 30 minutes at room temperature, and subsequently heated to 70-100° C., and volatile components, particularly air and excess amine, were removed under a vacuum. For the transimination, an aminosilane was subsequently added at room temperature, the reaction mixture was heated under thorough stirring to 80° C., and the pressure was reduced stepwise to 20-50 mbar until bubble formation had ceased, then the temperature was raised further to 120° C., and the pressure was reduced further to 0.05 mbar, again until bubble formation had ceased. The resulting iminosilane was cooled to room temperature and stored with exclusion of moisture.

Example 1

Iminosilane I-1

3-(2,2-dimethyl-3-(N-morpholino)propylidene-amino)propyltrimethoxysilane 17.98 g 2,2-dimethyl-3-(N-morpholino)propanal, 7.45 g 2-propanamine and 17.93 g 3-aminopropyltrimethoxysilane were reacted according to the general manufacturing procedure (iminosilanes). Yield: 32.2 g of a clear, yellowish oil with an amine content of 9.29 mmol N/g and a purity of 92%.

FT-IR: 2955, 2938, 2920 sh, 2837, 2809 sh, 1664 ($v_{C=N}$), 1454, 1410, 1396, 1375, 1360, 1345 sh, 1318, 1303, 1282, 1267, 1189, 1135, 1116, 1080, 1036, 1012, 930, 864, 815, 801, 775, 677.

$^1$H-NMR (CDCl$_3$, 300 K): δ 7.54 (t, J=1.2, 1H, CH=N), 3.64 (t, J=4.7, 4H, OCH$_2$CH$_2$N), 3.57 (s, 9H, Si(OCH$_3$)$_3$), 3.35 (t×d, J=7.0/1.1, 2H, CH=NCH$_2$), 2.46 (t, J=4.7, 4H, OCH$_2$CH$_2$N), 2.34 (s, 2H, NCH$_2$C(CH$_3$)$_2$), 1.68 (m, 2H, CH=NCH$_2$CH$_2$CH$_2$Si), 1.06 (s, 6H, C(CH$_3$)$_2$), 0.60 (m, 2H, CH=NCH$_2$CH$_2$CH$_2$Si).

Example 2

Iminosilane I-2

3-(2,2-dimethyl-3-(N,N-dimethylamino)propylidene-amino)propyltrimethoxysilane 13.57 g 2,2-dimethyl-3-dimethylaminopropanal, 7.45 g 2-propanamine and 17.93 g 3-aminopropyltrimethoxysilane were reacted according to the general manufacturing procedure (iminosilanes). The product was distilled after manufacture in order to remove oligomer portions. Yield: 28.4 g of a clear, colorless oil having an amine content of 6.61 mmol N/g and a purity of 95%.

FT-IR: 2938, 2837, 2828, 2766, 1665 ($v_{C=N}$), 1455, 1411, 1388, 1363, 1342, 1301, 1264, 1189, 1082, 1042, 906, 872, 844, 814, 775, 676.

$^1$H-NMR (CDCl$_3$, 300 K): δ 7.57 (t, J=1.2, 1H, CH=N), 3.56 (s, 9H, Si(OCH$_3$)$_3$), 3.37 (t×d, J=7.0/1.2, 2H, CH=NCH$_2$), 2.32 (s, 2H, NCH$_2$C(CH$_3$)$_2$), 2.23 (s, 6H, N(CH$_3$)$_2$), 1.69 (m, 2H, CH=NCH$_2$CH$_2$CH$_2$Si), 1.07 (s, 6H, C(CH$_3$)$_2$), 0.62 (m, 2H, CH=NCH$_2$CH$_2$CH$_2$Si).

Example 3

Iminosilane I-3

3-(2,2-Dimethyl-3-(N,N-dimethylamino)propylideneamino)propyltriethoxysilane 13.57 g 2,2-dimethyl-3-dimethylaminopropanal, 7.45 g 2-propanamine and 22.14 g 3-aminopropyltriethoxysilane were reacted according to the general manufacturing procedure (iminosilanes). Yield: 32.3 g of a clear, colorless oil having an amine content of 5.97 mmol N/g and a purity of 98%.

FT-IR: 2970, 2926, 2882, 2817, 2765, 1883 br, 1665 ($v_{C=N}$), 1466 sh, 1454, 1442, 1410, 1389, 1364, 1341, 1296, 1264, 1250 sh, 1181 sh, 1165, 1101, 1075, 1042, 993, 954, 867, 845, 809 sh, 791 sh, 774, 678.

$^1$H-NMR (CDCl$_3$, 300 K): δ 7.57 (t, J=1.2, 1H, CH=N), 3.81 (q, J=7.0, 6H, Si(OCH$_2$CH$_3$)$_3$), 3.37 (t×d, J=7.0/1.2, 2H, CH=NCH$_2$), 2.32 (s, 2H, NCH$_2$C(CH$_3$)$_2$), 2.23 (s, 6H, N(CH$_3$)$_2$), 1.70 (m, 2H, CH=NCH$_2$CH$_2$CH$_2$Si), 1.22 (t, J=7.0, 9H, Si(OCH$_2$CH$_3$)$_3$), 1.07 (s, 6H, C(CH$_3$)$_2$), 0.60 (m, 2H, CH=NCH$_2$CH$_2$CH$_2$Si).

Example 4

Iminosilane I-4

N-(2-(2,2-Dimethyl-3-(N-morpholino)propylidene-amino)ethyl)-3-aminopropyltrimethoxysilane)

17.98 g 2,2-Dimethyl-3-(N-morpholino)propanal, 7.45 g 2-propanamine and 22.24 g N-(2-aminoethyl)-3-aminopropyltrimethoxysilane were reacted according to the general manufacturing procedure (iminosilanes). Yield: 36.8 g of a clear, yellowish oil having an amine content of 8.04 mmol N/g and a purity of 95%.

FT-IR: 3310 ($v_{NH}$), 2941, 2888, 2865 sh, 2837, 2802, 1664 ($v_{C=N}$), 1454, 1410, 1395, 1374, 1358, 1345, 1315, 1281, 1265, 1189, 1133 sh, 1114, 1079, 1036, 1011, 922, 882, 864, 812, 805, 776 sh, 758 sh.

$^1$H-NMR (CDCl$_3$, 300 K): δ 7.61 (t, J=1.2, 1H, CH=N), 3.64 (t, J=4.6, 4H, OCH$_2$CH$_2$N), 3.57 (s, 9H, Si(OCH$_3$)$_3$), 3.49 (t×d, J=4.8/1.2, 2H, CH=NCH$_2$), 2.81 (t, J=4.8, 2H, CH=NCH$_2$CH$_2$NH), 2.62 (t, J=7.3, 2H, NHCH$_2$CH$_2$CH$_2$Si), 2.47 (t, J=4.6, 4H, OCH$_2$CH$_2$N), 2.35 (s, 2H, NCH$_2$C(CH$_3$)$_2$), 1.59 (m, 3H, NHCH$_2$CH$_2$CH$_2$Si and NH), 1.06 (s, 6H, C(CH$_3$)$_2$), 0.64 (m, 2H, NHCH$_2$CH$_2$CH$_2$Si).

4. Manufacture of Aminosilanes of Formula (I)

General Manufacturing Procedure (Hydrogenation)

In a round-bottom flask, an iminosilane was dissolved in sufficient isopropanal, and hydrogenated at a hydrogen pressure of 80 bar, a temperature of 80° C., and a flow rate of 3 mL/min in a continuously running hydrogenation apparatus with Pd/C solid bed catalyst. For the reaction control, a verification by IR spectroscopy was carried out to determine whether the imine bands at approximately 1665 cm$^{-1}$ had disappeared. Subsequently the solution was reduced in a vacuum at 80° C.

Example 5

Aminosilane A-1

3-(2,2-Dimethyl-3-(N-morpholino)propylamino) propyltrimethoxysilane

According to the general manufacturing procedure (hydrogenation), 10 g iminosilane I-1 of Example 1 were hydrogenated. The product was a clear, yellow, odorless oil having an amine content of 5.93 mmol N/g, which was successfully stored for a longer duration without decomposition.

FT-IR: 2940m, 2889m, 2837m, 2800m, 2677vw, 1465m sh, 1455m, 1411vw, 1396vw, 1373m, 1358w, 1318w, 1305w, 1283w, 1264w, 1190s, 1114s, 1080vs, 1037m, 1011s, 932w, 863s, 814s sh, 804s, 782s, 681w.

$^1$H-NMR (CDCl$_3$, 300 K): δ 3.66 (t, J=4.6, 4 H, OCH$_2$CH$_2$N), 3.57 (s, 9H, Si(OCH$_3$)$_3$), 2.57 (t, J=7.2, 2H, NHCH$_2$CH$_2$CH$_2$Si), 2.51 (t, J=4.6, 4H, OCH$_2$CH$_2$N), 2.40 (s, 2H, NCH$_2$C(CH$_3$)$_2$), 2.17 (s, 2H, NHCH$_2$C(CH$_3$)$_2$), 1.58 (m, 2H, NHCH$_2$CH$_2$CH$_2$Si), 1.3 (br s, 1H, NH), 0.87 (s, 6H, C(CH$_3$)$_2$), 0.65 (m, 2H, NHCH$_2$CH$_2$CH$_2$Si).

Example 6

Aminosilane A-2

3-(2,2-Dimethyl-3-(N-morpholino)propylamino) propyltrimethoxysilane

According to the general manufacturing procedure (hydrogenation), 10 g iminosilane I-2 of Example 2 were hydrogenated. The product was a clear, colorless and odorless oil having an amine content of 6.49 mmol N/g, which was successfully stored for a longer period without decomposition.

FT-IR: 2971m sh, 2939s, 2867m, 2837m, 2814m, 2763m, 1885vw br, 1463m sh, 1454m, 1410w, 1387w, 1373w, 1359w, 1303w, 1268m, 1189s, 1150m, 1084vs sh, 1080vs, 1043s, 868m, 815s, 778s, 761s sh, 679w.

$^1$H-NMR (CDCl$_3$, 300 K): δ 3.57 (s, 9H, Si(OCH$_3$)$_3$), 2.58 (t, J=7.2, 2H, NHCH$_2$CH$_2$CH$_2$Si), 2.41 (s, 2H, NCH$_2$C(CH$_3$)$_2$), 2.27 (s, 6H, N(CH$_3$)$_2$), 2.15 (s, 2H, NHCH$_2$C(CH$_3$)$_2$), 1.58 (m, 2H, NHCH$_2$CH$_2$CH$_2$Si), 1.2 (br s, 1H, NH), 0.89 (s, 6H, C(CH$_3$)$_2$), 0.66 (m, 2H, NHCH$_2$CH$_2$CH$_2$Si).

Example 7

Aminosilane A-3

3-(2,2-Dimethyl-3-(N-morpholino)propylamino) propyltriethoxysilane

According to the general manufacturing procedure (hydrogenation), 10 g iminosilane I-3 of Example 3 were hydrogenated. The product was a clear, yellow, odorless oil having an amine content of 5.99 mmol N/g, which was successfully stored for a longer period without decomposition.

FT-IR: 2970m, 2937m sh, 2926m, 2881m, 2814m, 2764m, 2730w sh, 1880vw br, 1465m sh, 1454m, 1443m, 1410w, 1389m, 1362w, 1295w, 1263w, 1166m, 1101s, 1075vs, 1043s, 953s, 845m, 775s, 680w.

$^1$H-NMR (CDCl$_3$, 300 K): δ 3.82 (q, J=7.0, 6H, Si(OCH$_2$CH$_3$)$_3$), 2.58 (t, J=7.2, 2H, NHCH$_2$CH$_2$CH$_2$Si), 2.41 (s, 2H, NCH$_2$C(CH$_3$)$_2$), 2.27 (s, 6H, N(CH$_3$)$_2$), 2.15 (s, 2H, NHCH$_2$C(CH$_3$)$_2$), 1.59 (m, 2H, NHCH$_2$CH$_2$CH$_2$Si), 1.23 (t, J=7.0, 9H, Si(OCH$_2$CH$_3$)$_3$), 1.1 (br s, 1H, NH), 0.89 (s, 6H, C(CH$_3$)$_2$), 0.63 (m, 2H, NHCH$_2$CH$_2$CH$_2$Si).

5. Manufacture of Silane Functional Polymers

Examples 8-11 and Comparison Examples 12-14

For each example, 100 parts by weight of the polyurethane polymer indicated in Table 1 ("PU polymer P-1" or "PU polymer P-2") were placed under a nitrogen atmosphere, the aminosilane indicated in the table was added in the indicated quantity (in parts by weight) through a dripping funnel under thorough stirring, and stirred at room temperature until no free isocyanate was detected any longer by IR spectroscopy. The product was stored with exclusion of moisture.

PU-Polymer P-1

Under a nitrogen atmosphere, 500.0 g Polyol Acclaim® 12200 (Bayer; low monol polyoxypropylene diol, OH number 11.0 mg KOH/g, water content approximately 0.02 wt %), 22.0 g isophorone diisocyanate (Vestanat® IPDI, Degussa) and 0.05 g di-n-butyltin dilaurate were heated under continuous stirring to 90° C. and left at this temperature until the content of free isocyanate groups, determined by titrimetry, had reached a value of 0.75 wt %. The product was cooled to room temperature and stored with exclusion of humidity. The viscosity at 20° C. was 40 Pa·s.

PU-Polymer P-2

Under a nitrogen atmosphere, 500.0 g Polyol Acclaim® 12200 (Bayer; low monol polyoxypropylene diol, OH number 11.0 mg KOH/g, water content approximately 0.02 wt %), 24.4 g tetramethyl-m-xylylene diisocyanate (TMXDI, Cytec) and 0.05 g di-n-butyltin dilaurate were heated under continuous stirring to 90° C. and left at this temperature until the content of free isocyanate groups, determined by titrimetry, had reached a value of 0.80 wt %. The product was cooled to room temperature and stored with exclusion of moisture. The viscosity at 20° C. was 55 Pa·s.

TABLE 1

Composition and viscosity of Examples 8-11 and of Comparison Examples 12-14.

| | Example | | | | | | |
|---|---|---|---|---|---|---|---|
| | 8 | 9 | 10 | 11 | 12 (comp.) | 13 (comp.) | 14 (comp.) |
| PU-Polymer P-1 | 100.00 | 100.00 | — | — | 100.00 | 100.00 | — |
| PU-Polymer P-2 | — | — | 100.00 | 100.00 | — | — | 100.00 |
| Aminosilane A-1 | 6.49 | — | 6.58 | — | — | — | — |
| Aminosilane A-2 | — | — | — | 6.00 | — | — | — |
| Aminosilane A-3 | — | 6.42 | — | — | — | — | — |
| 3-Aminopropyltrimethoxysilane$^a$ | — | — | — | — | 3.45 | — | — |
| N-(3-Trimethoxysilylpropyl) aminosuccinic acid diethyl ester$^b$ | — | — | — | — | — | 6.76 | 6.85 |
| Viscosity 20° C. [Pa · s] | 109 | 137 | 142 | 142 | 149 | 81 | 155 |

"comp" stands for "comparison"
$^a$Silquest ® A-1110, GE Advanced Materials
$^b$Adduct of $^a$ and maleic acid diethyl ester, described in U.S. Pat. No. 5,364,955, for example.

It can be seen from Table 1 that the presently disclosed silane functional polymers of Examples 8-11 have a lower viscosity than the silane functional polymers of the Comparison Example 12, which is derived from the corresponding primary aminosilane.

6. Manufacture of Moisture Curing Compositions

Examples 15-18 and Comparison Examples 19-21

For each example, the ingredients indicated in Table 2 were mixed in the indicated quantities (in parts by weight) using a centrifugal mixer (SpeedMixer™ DAC 150, FlackTek Inc.). For the resulting compositions, the appearance ("composition appearance") was evaluated, and the skin formation time ("SFT") in the standard climate (23±1° C., 50±5% relative air humidity) was determined as a measure of the curing rate. For this purpose, a few grams of the composition at room temperature were applied in a layer thickness of approximately 2 mm onto cardboard, and, in standard climate, the time was determined that it took until no residues remained on the pipette after slightly touching the surface of the adhesive with a pipette made of LDPE. Moreover, three films of each one of the compositions were applied with a layer thickness of 2 mm and cured for 14 days in the standard climate. The appearance ("film appearance NK") of one film of each was determined, and the tensile strength, the elongation at rupture, and the E modulus at 0.5-5% elongation were determined according to DIN 53504 (pulling rate: 200 mm/min) (values marked with "(NK)" in the table).

The second film in each case was stored, after the curing, for 7 days in the standard climate at 70° C. and 100% relative humidity, and then the tensile strength, the elongation at rupture and the E modulus at 0.5-5% elongation were determined in the same manner (values marked with "(70/100)" in the table). The third film in each case was stored, after the curing in the standard climate at 90° C. for 7 days, and then the tensile strength, the elongation at rupture, and the modulus at 0.5-5% elongation were determined in the same manner (values marked with "(90° C.)" in the table). Finally, the appearance of this film was evaluated ("appearance film 90° C.").

The results are indicated in Table 2.

As can be seen in Table 2, the skin formation times of presently disclosed Examples 15 and 18 with the silane functional polymers of Examples 8 and 11, which comprise trimethoxysilane groups and morpholino groups, were clearly shorter than those of Comparison Examples 20 and 21, which contained the silane functional polymers of Comparison Examples 13 and 14 based on the previously known secondary trimethoxyaminosilane, is presumably explained by a catalytic effect of the morpholino groups. Within 14 days, the compositions cured to transparent films with the expected mechanical properties of unfilled silane crosslinking compositions. Presently disclosed Examples 15, 17 and 18 all had nontacky films, while Comparison Examples 20 and 21, which in each case contained a silane crosslinking polymer with the known secondary aminosilanet, had a slightly tacky surface. The differences in the surface tackiness became very

TABLE 2

Properties of Examples 15-18 and of Comparison Examples 19-21.

| | Example | | | | | | |
|---|---|---|---|---|---|---|---|
| | 15 | 16 | 17 | 18 | 19 (comp.) | 20 (comp.) | 21 (comp.) |
| Polymer from example/ Quantity | 8/ 100 | 9/ 100 | 10/ 100 | 11/ 100 | 12/ 100 | 13/ 100 | 14/ 100 |
| Dibutyltin dilaurate | 0.08 | 0.08 | 0.08 | 0.08 | 0.08 | 0.08 | 0.08 |
| N-(2-Aminoethyl)-3-aminopropyltrimethoxysilane | 0.5 | 0.5 | 0.5 | 0.5 | 0.5 | 0.5 | 0.5 |
| Composition appearance | clear | clear | clear | clear | (clear)[a] | clear | Clear |
| SFT [min] | 85 | (30 h) | 89 | 140 | 37 | 100 | 127 |
| NK film appearance | colorless, nontacky | colorless, tacky | colorless, nontacky | colorless, nontacky | colorless, nontacky | colorless, slightly tacky | colorless, slight tacky |
| Tensile strength (NK) [MPa] (70/100) (90° C.) | 0.76 0.73 0.70 | 0.49 1.00 0.96 | 0.76 0.64 0.51 | 0.70 0.65 0.57 | 0.85 0.74 0.61 | 0.64 0.63 0.47 | 0.61 0.57 0.43 |
| Elongation at rupture (NK) [%] (70/100) (90° C.) | 75 87 103 | 166 158 140 | 85 95 121 | 72 114 132 | 66 63 59 | 107 122 106 | 124 156 186 |
| E modulus (NK) [MPa] (70/100) (90° C.) | 1.64 1.28 1.23 | 0.78 1.05 1.34 | 1.54 1.25 0.73 | 1.46 1.23 0.67 | 2.10 1.83 1.53 | 1.24 0.84 0.62 | 1.03 0.53 0.34 |
| Appearance film 90° C. | colorless, nontacky | colorless, slightly tacky | colorless, nontacky | colorless, nontacky | colorless, almost nontacky | yellow, tacky | yellow, tacky |

[a] Slightly inhomogeneous
"comp." stands for "comparison"

evident after thermal loading at 90° C. The films of Comparison Examples 20 and 21 were yellowed and tacky, whereas the films of Examples 15, 17 and 18 remained colorless and nontacky. Comparison Example 19, which is derived from a primary aminosilane, was in fact only slightly tacky after the thermal loading, but it had a low pressure expansion which is expected for such systems, and which can be however, insufficient for many applications. Example 16 which crosslinks via triethoxysilane groups had a slow curing and was therefore still tacky after 14 days. However, during thermal loading, it continued to cure well, which can be seen both from the mechanical values and also from the decrease in tackiness.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. Aminosilane of formula (I)

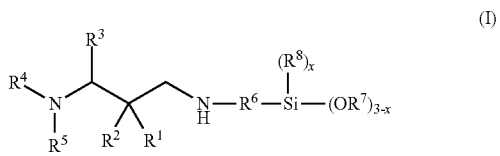

where
R$^1$ and R$^2$ either each stand, independently of each other, for a monovalent hydrocarbon residue having 1-12 C atoms, or together they stand for a bivalent hydrocarbon residue having 4-12 C atoms, which is part of an optionally substituted carbocyclic ring having 5-8 C atoms;
R$^3$ stands for a hydrogen atom or for an alkyl group or arylalkyl group or alkoxycarbonyl group each having 1-12 C atoms;
and either R$^4$ stands for a monovalent aliphatic, cycloaliphatic or arylaliphatic residue having 1-20 C atoms, which optionally contains heteroatoms, and R$^5$ stands for a hydrogen atom or for a monovalent, aliphatic, cycloaliphatic or arylaliphatic residue having 1-20 C atoms, which optionally contains heteroatoms,
or
R$^4$ and R$^5$ together stand for a bivalent aliphatic residue having 3-30 C atoms, which is part of an optionally substituted heterocyclic ring having 5-8 atoms, wherein this ring optionally contains further heteroatoms, besides a nitrogen atom;
R$^6$ stands for a linear or branched alkylene or cycloalkylene residue having 1-20 C atoms, optionally with aromatic portions, and optionally with one or more heteroatoms;
R$^7$ stands for an alkyl group having 1-10 C atoms, which optionally comprises ether oxygen, and two OR$^7$ groups together can stand for a bivalent glycolate group which forms a ring with the silicon atom;
R$^8$ stands for an alkyl group having 1-8 C atoms; and
x stands for 0, 1 or 2.

2. Aminosilane of formula (I) according to claim 1, wherein R$^1$ and R$^2$ each stand for a methyl residue and/or R$^3$ stands for a hydrogen atom.

3. Aminosilane of formula (I) according to claim 1, wherein either R$^4$ stands for methyl, ethyl, propyl, isopropyl, butyl, 2-ethylhexyl, cyclohexyl, 2-hydroxyethyl, 2-hydroxypropyl, 2-methoxyethyl or benzyl, and R$^5$ stands for hydrogen or methyl, ethyl, propyl, isopropyl, butyl, 2-ethylhexyl, cyclohexyl, 2-hydroxyethyl, 2-hydroxypropyl, 2-methoxyethyl or benzyl, or R$^4$ and R$^5$ together with the nitrogen atom form a ring, wherein this ring or the alkyl group is optionally substituted.

4. Aminosilane of formula (I) according to claim 1, wherein R$^6$ stands for a linear or branched alkylene residue having 1-6 C atoms.

5. Aminosilane of formula (I) according to claim 1, manufactured with an iminosilane of formula (II) configured for hydrogenation, wherein formula (II) is:

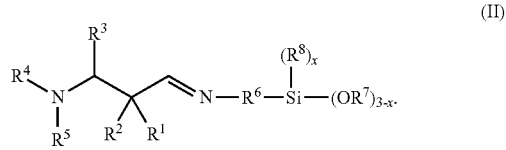

6. Method for manufacturing an iminosilane of formula (II):

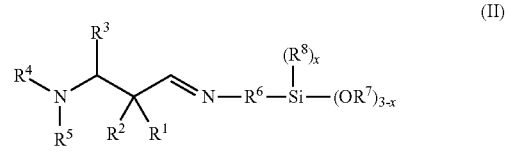

wherein at least one aminosilane AS of formula (III) is condensed with at least one aldehyde ALD of formula (IV), wherein formula (III) and formula (IV) are as follows:

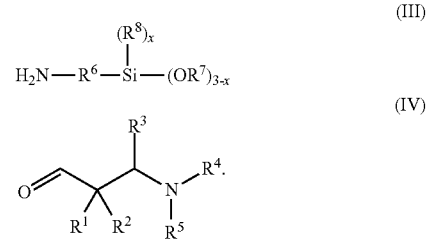

7. Method according to claim 6, comprising:
selecting the aminosilane AS of formula (III) from a group consisting of 3-aminopropyltrimethoxysilane, 3-aminopropyltriethoxysilane, 4-amino-3,3-dimethylbutyltrimethoxysilane, N-(2-aminoethyl)-3-aminopropyltrimethoxysilane and N-(2-aminoethyl)-3-aminopropyltriethoxysilane.

8. Method according to claim 6, comprising:
selecting the aldehyde ALD of formula (IV) from a group consisting of 2,2-dimethyl-3-methylaminopropanal, 2,2-dimethyl-3-dimethylaminopropanal, 2,2-dimethyl-3-ethylaminopropanal, 2,2-dimethyl-3-diethylaminopropanal, 2,2-dimethyl-3-bis(2-methoxyethyl)aminopropanal, 2,2-dimethyl-3-butylaminopropanal, 2,2-dimethyl-3-dibutylaminopropanal, 2,2-dimethyl-3-hexylaminopropanal, 2,2-dimethyl-3-(2-ethylhexyl)

aminopropanal, 2,2-dimethyl-3-dodecylaminopropanal, 2,2-dimethyl-3-(N-pyrrolidino)propanal, 2,2-dimethyl-3-(N-piperidino)propanal, 2,2-dimethyl-3-(N-morpholino)propanal, 2,2-dimethyl-3-(N-(2,6-dimethyl)morpholino)propanal, 2,2-dimethyl-3-benzylaminopropanal, 2,2-dimethyl-3-(N-benzylmethylamino)propanal, 2,2-dimethyl-3-(N-benzylisopropylamino)propanal, 2,2-dimethyl-3-cyclohexylaminopropanal, 2,2-dimethyl-3-(N-cyclohexylmethylamino)propanal and N,N'-bis(2,2-dimethyl-3-oxopropyl)piperazine.

9. Adduct AD, comprising:
a reaction product of at least one aminosilane of formula (I):

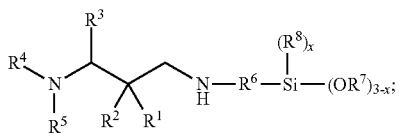

and
at least one compound VB which carries at least one reactive group RG, wherein the reactive group RG is selected from a group consisting of: isocyanate, isothiocyanate, cyclocarbonate, epoxide, episulfide, aziridine, acryl, methacryl, 1-ethinylcarbonyl, 1-propinylcarbonyl, maleimide, citraconimide, vinyl, isopropenyl and allyl groups; wherein:

$R^1$ and $R^2$ either each stand, independently of each other, for a monovalent hydrocarbon residue having 1-12 C atoms, or together they stand for a bivalent hydrocarbon residue having 4-12 C atoms, which is part of an optionally substituted carbocyclic ring having 5-8 C atoms;

$R^3$ stands for a hydrogen atom or for an alkyl group or arylalkyl group or alkoxycarbonyl group each having 1-12 C atoms;

and either $R^4$ stands for a monovalent aliphatic, cycloaliphatic or arylaliphatic residue having 1-20 C atoms, which optionally contains heteroatoms, and $R^5$ stands for a hydrogen atom or for a monovalent, aliphatic, cycloaliphatic or arylaliphatic residue having 1-20 C atoms, which optionally contains heteroatoms, or $R^4$ and $R^5$ together stand for a bivalent aliphatic residue having 3-30 C atoms, which is part of an optionally substituted heterocyclic ring having 5-8 atoms, wherein this ring optionally contains further heteroatoms, besides a nitrogen atom;

$R^6$ stands for a linear or branched alkylene or cycloalkylene residue having 1-20 C atoms, optionally with aromatic portions, and optionally with one or more heteroatoms;

$R^7$ stands for an alkyl group having 1-10 C atoms, which optionally comprises ether oxygen, and two $OR^7$ groups together can stand for a bivalent glycolate group which forms a ring with the silicon atom;

$R^8$ stands for an alkyl group having 1-8 C atoms; and x stands for 0, 1 or 2.

10. Adduct AD according to claim 9, wherein the reaction product is a silane functional polymer SP derived from the aminosilane of formula (I) and a compound VB that is a polyurethane polymer PUP bearing isocyanate groups.

11. Compound, comprising:
at least one silanol group of formula (IX), obtained from at least partial hydrolysis of at least one aminosilane of formula (I):

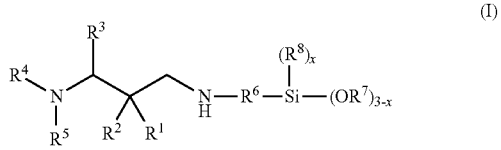

or of at least one iminosilane of formula (II):

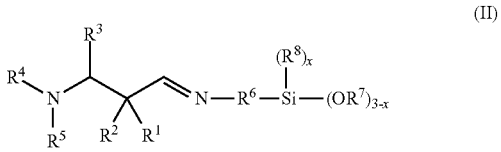

or of at least one adduct AD which includes a reaction product of at least one aminosilane of formula (I); and at least one compound VB which carries at least one reactive group RG, wherein the reactive group RG is selected from a group consisting of: isocyanate, isothiocyanate, cyclocarbonate, epoxide, episulfide, aziridine, acryl, methacryl, 1-ethinylcarbonyl, 1-propinylcarbonyl, maleimide, citraconimide, vinyl, isopropenyl and allyl groups;

wherein formula (IX) is as follows:

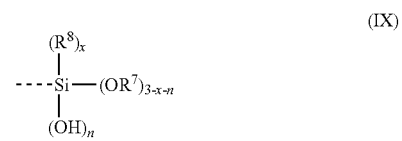

where n stands for 1 or 2 or 3, with a condition that n has at most a value (3-x); wherein:

$R^1$ and $R^2$ either each stand, independently of each other, for a monovalent hydrocarbon residue having 1-12 C atoms, or together they stand for a bivalent hydrocarbon residue having 4-12 C atoms, which is part of an optionally substituted carbocyclic ring having 5-8 C atoms;

$R^3$ stands for a hydrogen atom or for an alkyl group or arylalkyl group or alkoxycarbonyl group each having 1-12 C atoms;

and either $R^4$ stands for a monovalent aliphatic, cycloaliphatic or arylaliphatic residue having 1-20 C atoms, which optionally contains heteroatoms, and $R^5$ stands for a hydrogen atom or for a monovalent, aliphatic, cycloaliphatic or arylaliphatic residue having 1-20 C atoms, which optionally contains heteroatoms, or $R^4$ and $R^5$ together stand for a bivalent aliphatic residue having 3-30 C atoms, which is part of an optionally substituted heterocyclic ring having 5-8 atoms, wherein this ring optionally contains further heteroatoms, besides a nitrogen atom;

$R^6$ stands for a linear or branched alkylene or cycloalkylene residue having 1-20 C atoms, optionally with aromatic portions, and optionally with one or more heteroatoms;

R[7] stands for an alkyl group having 1-10 C atoms, which optionally comprises ether oxygen, and two OR[7] groups together can stand for a bivalent glycolate group which forms a ring with the silicon atom;

R[8] stands for an alkyl group having 1-8 C atoms; and x stands for 0, 1 or 2.

12. An adhesion promoting agent, accelerator and/or drying agent, for coating surfaces or as a component of curable materials, activators or primers comprising the aminosilane of formula (I) according to claim 1.

13. Composition containing at least one aminosilane of formula (I) according to claim 1.

14. Moisture curing composition, comprising:

at least one silane functional polymer SP according to claim 10; and at least one additional component.

15. A fiber composite, resilient casting compound, sealant, adhesive, covering, coating or paint for building and industry applications, or a foamed material comprising the moisture curing composition according to claim 14.

16. Aminosilane of formula (I) according to claim 1, wherein R[1] and R[2], and R[4] and R[5] comprise:

a substituted carbocyclic ring having 6 C atoms, and R[6] includes nitrogen atoms.

17. Aminosilane of formula (I) according to claim 2, wherein either R[4] stands for methyl, ethyl, propyl, isopropyl, butyl, 2-ethylhexyl, cyclohexyl, 2-hydroxyethyl, 2-hydroxypropyl, 2-methoxyethyl or benzyl, and R[5] stands for hydrogen or methyl, ethyl, propyl, isopropyl, butyl, 2-ethylhexyl, cyclohexyl, 2-hydroxyethyl, 2-hydroxypropyl, 2-methoxyethyl or benzyl, or R[4] and R[5] together with the nitrogen atom form a ring, wherein this ring or the alkyl group is optionally substituted.

18. Aminosilane of formula (I) according to claim 3, wherein R[4] and R[5] form a pyrrolidine, piperidine, morpholine or N-alkylpiperazine ring.

19. Aminosilane of formula (I) according to claim 18, wherein R[6] stands for a linear or branched alkylene residue having 1-6 C atoms, or for a linear alkylene residue having 5-7 C atoms, which has one or 2 secondary amino groups in the chain for a —$(CH_2)_2$—NH—$(CH_2)_3$— or for a —$(CH_2)_2$—NH—$(CH_2)_2$—NH—$(CH_2)_3$— residue.

20. Aminosilane of formula (I) according to claim 4, wherein R[6] includes a propylene group, or is a linear alkylene residue having 5-7 C atoms, which has one or 2 secondary amino groups in the chain for a —$(CH_2)_2$—NH—$(CH_2)_3$— or for a —$(CH_2)_2$—NH—$(CH_2)_2$—NH—$(CH_2)_3$— residue.

* * * * *